US008144966B2

(12) United States Patent
Provenzano et al.

(10) Patent No.: US 8,144,966 B2
(45) Date of Patent: Mar. 27, 2012

(54) USE OF ENDOGENOUS FLUORESCENCE TO IDENTIFY INVADING METASTATIC BREAST TUMOR CELLS

(75) Inventors: Paolo P. Provenzano, Madison, WI (US); Patricia Jo Keely, Madison, WI (US); Kevin W. Eliceiri, Madison, WI (US); John G. White, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 999 days.

(21) Appl. No.: 12/040,013

(22) Filed: Feb. 29, 2008

(65) Prior Publication Data

US 2008/0212867 A1 Sep. 4, 2008

Related U.S. Application Data

(60) Provisional application No. 60/892,687, filed on Mar. 2, 2007.

(51) Int. Cl.
*A61B 5/00* (2006.01)
*G06K 9/00* (2006.01)
(52) U.S. Cl. ........................................ 382/133; 600/477
(58) Field of Classification Search .................. 382/128, 382/131, 133
See application file for complete search history.

(56) References Cited

U.S. PATENT DOCUMENTS

| | | | |
|---|---|---|---|
| 5,769,081 A | 6/1998 | Alfano et al. | |
| 6,580,941 B2 | 6/2003 | Webb | |
| 6,615,063 B1 | 9/2003 | Ntziachristos et al. | |
| 6,687,000 B1 | 2/2004 | White | |
| 6,720,547 B1 | 4/2004 | Rajadhyaksha et al. | |
| 6,839,586 B2 | 1/2005 | Webb | |
| 6,879,394 B2 | 4/2005 | Amblard et al. | |
| 6,889,075 B2 | 5/2005 | Marchitto et al. | |
| 2003/0013973 A1* | 1/2003 | Georgakoudi et al. | 600/473 |
| 2003/0017111 A1 | 1/2003 | Rabito | |
| 2004/0206882 A1* | 10/2004 | Banks et al. | 250/201.2 |
| 2004/0209237 A1* | 10/2004 | Flewelling et al. | 435/4 |
| 2005/0259249 A1 | 11/2005 | Dombeck et al. | |
| 2006/0089556 A1* | 4/2006 | Bambot et al. | 600/476 |
| 2007/0161876 A1* | 7/2007 | Bambot et al. | 600/310 |
| 2007/0213618 A1* | 9/2007 | Li et al. | 600/476 |
| 2008/0015448 A1 | 1/2008 | Keely et al. | |

OTHER PUBLICATIONS

Becker and Bergmann, "Lifetime Imaging Techniques for Optical Microscopy", Becker & Hickel GmbH, Berlin, http://www.becker-hickl.de/pdf/tcvgbh1.pdf, 2003.*
Abramoff et al. (Jul. 2004) "Image Processing With ImageJ," *Biophotonics Int.* 11:36-42.
Ada-Nguema et al. (2006) "The Small GTPase R-Ras Regulates Organization of Actin and Drives Membrane Protrusions Through the Activity of PLC{epsilon}," *J. Cell Sci.* 119(7):1307-1319.

(Continued)

*Primary Examiner* — Jack Berman
*Assistant Examiner* — David E Smith
(74) *Attorney, Agent, or Firm* — Greenlee Sullivan P.C.

(57) ABSTRACT

The present invention broadly provides methods and systems for detecting, identifying, and characterizing conditions, including diseases and other disorders in human or other animal subjects, by analyzing fluorescence from endogenous flavin adenine dinucleotide (FAD) fluorophors present in biological materials and samples. In particular embodiments, the invention relates to conditions of the human breast including cancers such as carcinoma. Methods and systems are provided for detecting, locating, and characterizing tumors and precancerous tissue via nonlinear optical imaging techniques capable of accurately characterizing fluorescence intensities and fluorescent lifetime parameters from endogenous FAD fluorophors present in a test tissue sample.

27 Claims, 17 Drawing Sheets

OTHER PUBLICATIONS

Aiello et al. (Mar. 2005) "Association Between Mammographic Breast Density and Breast Cancer Tumor Characteristics," *Cancer Epidemiol Biomarl. Prev.* 14:662-668.

Allinen et al. (Jul. 2004) "Molecular Characterization of the Tumor Microenvironment in Breast Cancer," *Cancer Cell.* 6:17-32.

Alowami et al. (203) "Mammographic Density is Related to Stroma and Stromal Proteoglycan Expression," *Breast Cancer Res.* 5:R129-R135.

Aplin et al. (1999) "Integrin and Cytoskeletal Regulation of Growth Factor Signaling to the MAP Kinase Pathway," *J. Cell. Sci.* 112(5):695-706.

Baba et al. (2006) "Syndecan-1 and Syndecan-4 are Overexpressed in an Estrogen Receptor-Negative, Highly Proliferative Breast Carcinoma Subtype," *Breast Cancer Res. Treat.* 98:91-98.

Barcellos-Hoff et al. (1989) "Functional Differentiation and Alveolar Morphogenesis of Primary Mammary Cultures on Reconstituted Basement Membrane," *Development* 105:223-235.

Baron et al. (Mar. 20, 1998) "p125Fak Focal Adhesion Kinase is a Substrate for the Insulin and Insulin-Like Growth Factor-I Tyrosine Kinase Receptors," *J. Biol. Chem.* 273:7162-7168.

Barsky et al. (1982) "Increased Content of Type V Collagen in Desmoplasia of Human Breast Carcinoma," *Am. J. Pathol.* 108:276-283.

Bavik et al. (Jan. 15, 2006) "The Gene Expression Program of Prostate Fibroblast Senescence Modulates Neoplastic Epithelial Cell Proliferation Through Paracrine Mechanisms," *Cancer Res.* 66:794-802.

Becker et al. (2004) "Fluorescence Lifetime Imaging by Time-Correlated Single-Photon Counting," *Microsc. Res. Tech.* 63(1):58-66.

Benlimame et al. (Nov. 7, 2005) "FAK Signaling is Critical for ErbB-2/ErbB-3 Receptor Cooperation for Oncogenic Transformation and Invasion," *J. Cell. Biol.* 171:505-516.

Bird et al. (Sep. 2004) "Simultaneous Two-Photon Spectral and Lifetime Fluorescence Microscopy," *Appl. Opt.* 43:5173-5182.

Bird et al. (Oct. 2002) "Fibre-Optic Two-Photon Scanning Fluorescence Microscopy," *J. Microsc.* 208:33-48.

Bird et al. (Apr. 2002) "Resolution Improvement in Two-Photon Fluorescence Microscopy with a Single-Mode Fiber," *Appl. Opt.* 41:1852-1857.

Bird et al. (Sep. 2003) "Two-Photon Fluorescence Endoscopy with a Micro-Optic Scanning Head," *Opt. Lett.* 28:1552-1554.

Bird et al. (Oct. 2005) "Metabolic Mapping of MCF10A Human Breast Cells via Multiphoton Fluorescence Lifetime Imaging of the Coenzyme NADH," *Cancer Res.* 65(19):8766-8773.

Boyd et al. (Sep. 2002) "Heritability of Mammographic Density, A risk Factor for Breast Cancer," *N. Eng. J. Med.* 347:886-894.

Boyd et al. (Dec. 1998) "Mammographic Densities and Breast Density Cancer Risk," *Cancer Epidemiology Biomark. Prev.* 7:1133-1144.

Boyd et al. (2001) "Mammographic Densities as a marker of Human Breast Cancer Risk and Their use in Chemoprevention," *Curr. Oncol. Rep.* 3:314-321.

Boyd et al. (Oct. 2005) "Mammographic Breast Density as an Intermediate Phenotype for Breast Cancer," *Lancet. Oncol.* 6:798-808.

Boyd et al. (2002) "The Association of Breast Mitogens with Mammographic Densities," *Br. J. Cancer* 87:876-882.

Brakenhoff et al. (Oct. 1985) "Three-Dimensional Chromatin Distribution in Neuroblastoma Nuclei Shown by Confocal Scanning Laser Microscopy," *Nature* 317(6039):748-749.

Brown et al. (Jun. 2003) "Dynamic Imaging of Collagen and its Modulation in Tumors in Vivo Using Second-Harmonic Generation," *Nat. Med.* 9:796-800.

Brown et al. (Jul. 2001) "In Vivo Measurement of Gene Expression, Angiogenesis and Physiolgical Function in Tumors Using Multiphoton Laser Scanning Microscopy," *Nat. Med.* 7:864-868.

Byrne et al. (Jul. 2000) "Plasma Insulin-Like Growth Factor (IGF) I, IGF-Binding Protein 3, and Mammographic Density," *Cancer Res.* 60:3744-3748.

Campagnola et al. (Jul. 2001) "Second-Harmonic Imaging Microscopy of Living Cells," *J. Biomed. Opt.* 6:277-286.

Campagnola et al. (Jan. 2002) "Three-Dimensional High-Resolution Second-Harmonic Generation Imaging of Endogenous Structural Proteins in Biological Tissues," *Biohys. J.* 82:493-508.

Candes et al. (1999) "Curvelets—A Surprisingly Effective Non-Adaptive Representation for Objects with Edges," In; *Curve and Surface Fitting*, Vanderbilt University Press.

Candes et al. (Nov. 2002) "New Tight Frames of Curvelets and Optimal Representations of Objects with Smooth Singularities," *Technical Report*, Stanford University.

Centzone et al. (Oct. 1998) "Multiphoton Excitation Provides Optical Sections from Deeper Within Scattering Specimens than Confocal Imaging," *Biophys. J.* 75:2015-2024.

Chen et al. (Jul. 2002) "The $\alpha_2$ Integrin Subunit-Deficient Mouse," *Am. J. Pathol.* 161(1):337-344.

Chu et al. (Apr. 2003) "Real-Time Second-Harmonic-Generation Microscopy Based on a 2-GHz Repetition rate Ti:Sapphire Laser," *Optics Express* 11(8):933-938.

Chung et al. (Jan. 2005) "Molecular Insights into Prostate Cancer Progression: The Missing Link of Tumor Microenvironment," *J. Urol.* 173:10-20.

Condeelis et al. (2005) "The Great Escape: When Cancer Cells Hijack the Genes for Chemotaxis and Motility," *Ann. Rev. Cell. Dev. Biol.* 21:695-718.

Cornell News (Feb. 2004) "New Optical Recording Technique Can See Milli Second Nerve Impulses in Healthy and Diseased Brains, Cornell Biophysicists Report," http://www.news.cornell.edu/release/Feb04/Optical_recordings.hrs.html.

Cox et al. (2003) "3-Dimensional Imaging of Collagen Using Second Harmonic Generation," *J. Struct. Biol.* 141:53-62.

Cremazy et al. (2005) "Imaging in situ Protein-DNA Interactions in the Cell Nucleus Using FRET-FLIM," *Exp. Cell Res.* 309(2):390-396.

Croft et al. (Dec. 15, 2004) "Conditional ROCK Activation In vivo Induces Tumor Cell Dissemination and Angiogenesis," *Cancer Res.* 64:8994-9001.

DeMali et al. (2003) "Coupling Membrane Protrusion and Cell Adhesion," *J. Cell. Sci.* 116(12):2389-2397.

Denk et al. (Apr. 1990) "Two-Photon Laser Scanning Fluorescence Microscopy," *Science* 248:73-76.

DeWever et al. (2003) "Role of Tissue Stroma in Cancer Cell Invasion," *J. Pathol.* 200:429-447.

Diamant et al. (1972) "Collagen; Ultrastructure and its Relation to Mechanical Properties as a Function of Ageing," *Proc. Royal. Soc. Lond.* 180B:293-315.

Diaspro et al. (2002) "Two-Photon Excitation Fluorescence Microscopy," In; *Confocal and Two-Photon Microscopy: Foundations, Applications, and Advances*, Diaspro ed., Wiley-Liss, Inc. New York, pp. 39-73.

Donoho, D.L. (May 1995) "De-Noising by Soft-Thresholding," *IEEE Trans. Info. Theory*.

Elenbaa et al. (2001) "Human Breast Cancer Cells Generated by Oncogenic Transformation of Primary Mammary Epithelial Cells," *Genes. Dev.* 15:50-65.

Eliceiri et al. (2003) "Analysis of Histology Specimens Using Lifetime Multiphoton Microscopy," *J. Biomed. Opt.* 8:376-380.

Eliceiri et al. (2005) "Tools for Visualizing Multidimensional Images from Living Specimens," *Photochem. Photobiol.* 81:1116-1122.

Fata et al. (Aug. 19, 2003) "Regulation of Mammary Gland Branching Morphogenesis by the Extracellular Matrix and Its Remodeling Enzymes," *Breast Cancer Res.* 6:1-11.

Flusberg et al. (Dec. 2005) "Fiber-Optic Fluorescence Imaging," *Nat. Methods* 2:941-950.

French et al. (Mar. 1997) "Two-Photon Fluorescence Lifetime Imaging Microscopy of Macrophage-Mediated Antigen Processing," *J. Microsc.* 185(3):339-353.

Freund et al. (Feb. 1986) "Second-Harmonic Microscopy of Biological Tissue," *Optics Lett.* 11:94-96.

Friedl et al. (May 2003) "Tumour-Cell Invasion and Migration: Diversity and Escape Mechanisms," *Nat. Rev. Cancer* 3(5):362-374 *Nat. Rev. Cancer* 3:362-374.

Friedl et al. (2004) "Collective Cell Migration in Morphogenesis and Cancer," *Int. J. Dev. Biol.* 48:441-449.

Galeotti et al. (1970) "On the Fluorescence of NAD(P)H in Whole-Cell Preparations of Tumours and Normal Tissues," *Eur. J. Biochem.* 17(3):485-496.

Gill et al. (2006) "The Association of Mammographic Density with Ductoral Carcinoma in situ of the Breast Tissue: the Multiethnic Cohort," *Breast Cancer Res.* 8:R30.

Goldberg et al. (May 3, 2005) "The Open Microscopy Environment (OME) Data Model and XML File: Open Tools for Informatics and Quantitative Analysis in Biological Imaging," *Genome Biol.* 6(5):R47-.

Guo et al. (Sep. 1999) "Subsurface Tumor Progression Investigated by Noninvasive Optical Second Harmonic Tomography," *Proc. Nat. Acad. Sci. USA* 96(19):10854-10856.

Guo et al. (Mar. 2001) "Growth Factors and Stromal Matrix Proteins Associated with Mammographic Densities," *Cancer Epidemiol Biomark. Prev.* 10:243-248.

Habel et al. (Oct. 6, 2004) "Mammographic Density and Breast Cancer after Ductal Carcinoma in Situ," *J. Nat. Cancer Inst.* 96:1467-1472.

Hagios et al. (1998) "Tissue Architecture: The Ultimate Regulator of Epithelial Function," *Philos Trans. R. Soc. Lond. B. Biol. Sci.* 353:857-870.

Hanahan et al. (Jan. 7, 2000) "The Hallmarks of Cancer," *Cell.* 100(1):57-70.

Harpur et al. (Feb. 2001)"Imaging FRET Between Spectrally Similar GFP Molecules in Single Cells," *Nat. Biotechnol.* 19(2):167-169.

Hauck et al. (Oct. 1, 2001) "Inhibition of Focal Adhesion Kinase Expression or Activity Disrupts Epidermal Growth Factor-Stimulated Signaling Promoting the Migration of Invasive Human Carcinoma Cells," *Cancer Res.* 61:7079-7090.

Hawes et al. (206) "Dense Breast Stromal Tissue Shows Greatly Increased Concentration of Breast Epithelium but no Increase in its Proliferative Activity," *Breast Cancer Res.* 8:R24.

Hegerfeldt et al. (Apr. 1, 2002) "Collective Cell Movement in Primary Melanoma Explants: Plasticity of Cell-Cell Interaction, [beta]1-Integrin Function, and Migration Strategies," *Cancer Res.* 62(7):2125-2130.

Helmchen et al. (2002) "New Developments in Multphoton Microscopy," *Curr. Opin. Neurobiol.* 12:593-601.

Huang et al. (May 2002) "Two-Photon Fluorescence Spectroscopy and Microscopy of NAD(P)H and Flavoprotein," *Biophys. J.* 82:2811-2825.

Hurschler et al. (Jun. 2003) "Application of a Probabilistic Microstructural Model to Determine Reference Length and Toe-to-Linear Region Transition in Bibrous Connective Tissue," *ASME J. Biomech. Eng.* 125:415-422.

Ishizawar et al. (Sep. 2004) "c-Src and Cooperating Partners in Human Cancer," *Cancer Cell* 6:209-214.

Iyengar et al. (May 2005) "Adipocyte-Derived Collagen VI Affects Early Mammary Tumor Progression in Vivo, Demonstrating a Critical Interaction in the Tumor/Stroma Microenvironment," *J. Clin. Invest.* 115:1163-1176.

Jacks et al. (May 2002) "Taking the Study of Cancer Cell Survival to a New Dimension," *Cell* 111(7):923-925.

Jaffe et al. (2005) "RHO GTPases: Biochemistry and Biology," *Ann. Rev. Cell Dev. Biol.* 21(1):247-269.

Jain et al. (Apr. 2002) "Dissecting Tumour Pathophysiology Using Intravital Microscopy," *Nat. Rev. Cancer* 2(4):266-276.

Jiang et al. (May 15, 2004) "Second-Harmonic Optical Coherence Tomography," *Optics Lett.* 29(10):1090-1092.

Jung et al. (Jun. 1, 2003) "Mulitiphoton Endoscopy," *Opt. Lett.* 28:902-904.

Katz et al. (Feb. 2002) "Noninvasive Native Fluorescence Imaging of Head and Neck Tumors," *Technol. Cancer Res. Treat.* 1(1):9-15.

Keely et al. (1995) "Alteration of Collagen-Dependent Adhesion, Motility, and Morphogenesis by the Expression of Antisnese α2 Integrin mRNA in Mammary Cells," *J. Cell. Sci.* 108:595-607.

Keely et al. (Jul. 1995) "The Spatial and Temporal Expression of the α2β1 Integrin and its Ligands, Suggest Important Roles in Mouse Mammary Morphogenesis," *Differentiation* 59(1):1-13.

Keely et al. (May 31, 1999) "R-Ras Signals Through Specific Integrin Alpha Cytoplasmic Domains to Promote Migration and Invasion of Breast Epithelial Cells," *J. Cell Biol.* 145(5):1077-1088.

Kirkptrick et al. (2005) "Endogenous Fluorescence Spectroscopy of Cell Suspensions for Chemopreventive Drug Monitoring," *Photchem. Photobiol.* 81(1):125-134.

Lakowicz et al. (1992) "Fluorescence Lifetime Imaging," *Anal. Biochem.* 202(2):316-330.

Lee et al. (Sep. 2001) "Application of the Stretched Exponential Function to Fluorescence Lifetime Imaging," *Biophys. J.* 81(3):1265-1274.

Li et al. (2000) "Use of MMTV-*Wnt-1* Transgenic Mice for Studying the Genetic Basis of Breast Cancer," *Oncogene* 19:1002-1009.

Li et al. (Feb. 2005) "The Association of Measured Breast Tissue Characteristics with Mammographic Density and Other Risk Factors for Breast Cancer," *Cancer Epidemiol Biomark. Prev.* 14:343-349.

Lin et al. (Nov. 2003) "Progression to Malignancy in the Polyoma Middle T Oncoprotein Mouse Breast Cancer Model Provides a Reliable Model for Human Disease," *Am. J. Pathol.* 163:2113-2126.

Liotta et al. (Jan. 2003) "Cancer's Deadly Signature," *Nat. Genet.* 33:10-11.

Lippincott-Schwartz et al. (Jun. 2001) "Studying Protein Dynamics in Living Cells," *Nat. Rev. Mol. Cell Biol.* 2(6):444-456.

Lippincott-Schwartz et al. (Apr. 4, 2003) "Development and Use of Fluorescent Protein Makers in Living Cells," *Science* 300(5616):87-91.

Liu et al. (Jul. 1995) "A Targeted Mutation at the Known Collagenase Cleavage Site in Mouse Type 1 Collagen Impairs Tissue Remodeling," *J. Cell. Biol.* 130:227-237.

Lyengar et al. (May 2005) "Adipocyte-Derived Collagen VI Affects Early Mammary Tumor Progression in Vivo, Demonstrating a Critical Interaction in the Tumor/Stroma Microenvironment," *J. Clin. Invest.* 115:1163-1176.

Marsh et al. (May 19, 2003) "Practical Implementation of Adaptive Optics in Multiphoton Microscopy," *Opt. Express* 11:1123-1130.

McCormack et al. (Jun. 2006) "Breast Density and Parenchymal Patterns as Markers of Breast Cancer Risk; a Meta-Analysis," *Cancer. Epidemiol. Biomark. Prev.* 15:1159-1169.

McNeel et al. (Nov. 1, 2005) "Phase I Trial of a Monoclonal Antibody Specific for Alphavbeta3 Integrin (MEDI-522) in Patients with Advanced Malignancies, Including an Assessment of Effect on Tumor Perfusion," *Clin. Cancer Res.* 11:7851-7860.

Mohler et al. (2003) "Second Harmonic Generation Imaging of Endogenous Structural Proteins," *Methods* 29:97-109.

Monaghan et al. (Jun. 1983) "Topographical Arrangement of Basement Membrane Proteins in Lactating Rat Mammary Gland: Comparison of the Distribution of Type IV Collagen, Laminin, Fibronectin, and Thy-1 at the Ultrastructural Level," *Proc. Nat. Acad. Sci. USA* 80:3344-3348.

Muti, P. (2004) "The Role of Endogenous Hormones in the Etiology and Prevention of Breast Cancer: The Epidemiological Evidence," *Ann. N.Y. Acad. Sci.* 1028-273-282.

Noel et al. (1998) "The Role of Stroma in Breast Carcinoma Growth in Vivo," *J. Mam. Gland Biol. Neoplasia* 3:215-225.

Orima et al. (May 6, 2005) "Stromal Fibroblasts Present in Invasive Human Breast Carcinomas Promote Tumor Growth and Angiogenesis Through Elevated SDF-1/CXCL12 Secretion," *Cell* 121:335-348.

Oron et al. (Jul. 2004) "Depth-Resolved Structural Imaging by Third-Harmonic Generation Microscopy," *J. Struct. Biol.* 147(1):3-11.

Palmer et al. (2003) "Autofluorescence Spectroscopy of Normal and Malignant Human Breast Cell Lines," *Photochem. Photobiol.* 78(5):462-469.

Parr et al. (Jan. 1, 2004) "The Hepatocyte Growth Factor Regulatory Factors in Human Breast Cancer," *Clin. Cancer Res.* 10:202-21.

Parry et al. (1984) "Growth and Development of Collagen Fibrils in Connective Tissue," In; *Ultrastructure of the Connective Tissue Matrix*, Ruggeri et al. eds., The Hauge, Martinus Nijhoff, pp. 34-62.

Parsons et al. (Mar. 2005) "Spatially Distinct Binding of Cdc42 to PAK1 and N-WASP in Breast Carcinoma Cells," *Mol. Cell Biol.* 25(5):1680-1695.

Paszek et al. (Sep. 2005) "Tensional Homeostasis and the Malignant Phenotype," *Cancer Cell* 8:241-254.

Patterson et al. (May 9, 2000) "Separation of the Glucose-Stimulated Cytoplasmic and Mitochondrial NAD(P)H Responses in Pancreatic Islet Beta Cells," *Proc. Nat. Acad. Sci. USA* 97(10):5203-5207.

Peter et al. (2004) "Imaging Molecular Interactions by Multiphoton FLIM," *Biol. Cell* 96(3):231-236.
Peter et al. (Feb. 2005) "Multiphoton-FLIM Quantification of the EFP-mRFP1 FRET Pair for Localization of Membrane Receptor-Kinase Interactions," *Biophys. J.* 88(2):1224-1237.
Pitts et al. (Jan. 2001) "Autofluorescence Characteristics of Immortalized and Carcinogen-Transformed Human Bronchial Epithelial Cells," *J. Biomed Opt.* 6(1):31-40.
Plotnikov et al. (Jan. 2006) "Characterization of the Myosin-Based Source for Second-Harmonic Generation from Muscle Sarcomeres," *Biophys. J.* 90:693-703.
Poteryaev et al. (May 2005) "Involvement of the Actin Cytoskeleton and Homotypic Membrane Fusion in ER Dynamics in *Caenorhabditis elegans*," *Mol. Biol. Cell* 16(5):2139-2153.
Pradhan et al. (1995) "Steady State and Time-Resolved Fluorescence Properties of Metastic and Non-Metastic Malignant Cells from Different Species," *J. Photochem. Photobiol. B* 31:101-112.
Provenzano et al. (Dec. 26, 2006) "Collagen Reorganization at the Tumor-Stromal Interface Facilitates Local Invasion," *BMC Med.* 4:38.
Ramanujam, N. (2000) "Fluorescence Spectroscopy of Neoplastic and Non-Neoplastic Tissues," *Neoplasia* 2(1-2):89-117.
Rangarajan et al. (Aug. 2004) "Species- and Cell Type-Specific Requirements for Cellular Transformation," *Cancer Cell* 6(2):171-183.
Robu et al. (Nov. 28, 2003) "Localization of Functional Endothelin Receptor Signaling Complexes in Cardiac Transverse Tubules ," *J. Biol. Chem.* 278(48):48154-48161.
Ronnov-Jessen et al. (Feb. 1995) "The Origin of the Myofibroblasts in Breast Cancer. Recapitulation of Tumor Environment in Culture Unravels Diversity an Implicates Converted Fibroblasts and Recruited Smooth Muscle Cells," *J. Clin. Invest.* 95(2):859-873.
Rueden et al. (2004) "VisBio: A Computational Tool for Visualization of Multidimensional Biological Image Data," *Traffic* 5:411-417.
Rutter et al. (Jan. 10, 2001) "Changes in Breast Density Associated with Initiation, Discontinuation, and Continuing use of Hormone Replacement Therapy," *JAMA* 285:171-176.
Sachdev et al. (2001) "The IGF System and Breast Cancer," *Endocr. Relat. Cancer* 8:197-209.
Sahai et al. (2005) "Simultaneous Imaging of GFP, CFP and Collagen in Tumors in Vivo Using Multiphoton Microscopy," *BMC Biotechnol.* 5:14-.
Sato et al. (Oct. 1, 2004) "Gene Expression Profiling of Tumor-Stromal Interactions Between Pancreatic Cancer Cells and Stromal Fibroblasts," *Cancer Res.* 64(19):6950-6956.
Shekhar et al. (Feb. 2003) "Extracellular Matrix-Stromal Cell Contribution to Neoplastic Phenotype of Epithelial Cells in the Breast," *Breast Cancer Res.* 5(3):130-135.
Shen, Y.R. (Feb. 9, 1989) "Surface Properties Probed by Second-Harmonic and Sum-Frequency Generation," *Nature* 337:519-525.
Sieg et al. (May 2000) "FAK Integrates Growth-Factor and Integrin Signals to Promote Cell Migration," *Nat. Cell. Biol.* 2:249-256.
Skala et al. (Feb. 15, 2005) "Multiphoton Microscopy of Endogenous Fluorescence Differentiates Normal, Precancerous, and Cancerous Squamous Epithelial Tissues," *Cancer Res.* 65(4):1180-1186.
Squirrell et al. (Aug. 1999) "Long-Term Two-Photon Fluorescence Imaging of Mammalian Embryos Without Compromising Viability," *Nat. Biotechnol.* 17:763-767.
Squirrell et al. (Jan. 2006) "CAR-1, a Protein that Localizes with the mRNA Decapping Component DCAP-1, Is Required for Cytokinesis and ER Organization in *Caenorhabditis elegans* Embryos," *Mol. Biol. Cell.* 17(1):336-344.
Stoller et al. (Apr. 2002) "Polarization-Dependent Optical Second-Harmonic Imaging of a Rat-Tail Tendon," *J. Biomed. Opt.* 7:205-214.
Strome et al. (Jun. 2001) "Spindle Dynamics and Role of {Gamma}-Tubulin in Early *Caenorhabditis elegans* Embryos," *Mol. Biol. Cell* 12(6):1751-1764.
Sullivan et al. (2002) "Major Accomplishments for the Cancer Imaging Program," http://www.cancer.gov/dctd/cip_accomplishments.

Surmacz, E. (2002) "Function of the IGF-I Receptor in Breast Cancer," *J. Mamm. Gland Biol. Neoplasia* 5:95-105.
Tadrous et al. (2003) "Fluorescence Lifetime Imaging of Unstained Tissues: Early Results in Human Breast Cancer," *J. Pathol.* 199(3):309-317.
Tlsty et al. (2001) "Know thy Neighbor: Stromal Cells can Contribute Oncogenic Signals," *Curr. Opin. Genetic Dev.* 1:54-59.
Ursin et al. (2005) "Greatly Increased Occurrence of Breast Cancers in Areas of Mammographically Dense Tissue," *Breast Cancer Res.* 7:R605-R608.
van Munster et al. (2005) "Fluorescence Lifetime Imaging Microscopy (FLIM)," *Curr. Opin. Genet. Dev.* 11(1):54-59.
Verveer et al. (Nov. 24, 2000) "Quantitative Imaging of Lateral ErbB1 Receptor Signal Propagation in the Plasma Membrane," *Science* 290(5496):1567-1570.
Wang et al. (Dec. 1, 2004) "Identification and Testing of a Gene Expression Signature of Invasive Carcinoma Cells within Primary Mammary Tumors," *Cancer Res.* 64(23):8585-8594.
Wang et al. (Mar. 2005) "Tumor Cells Caught in the Act of Invading: Their Strategy for Enhanced Cell Motility," *Trends Cell Biol.* 15:138-145.
Wang et al. (Nov. 1, 2002) "Single Cell Behavior in Metastic Primary Mammary Tumors Correlated with Gene Expression Patterns Revealed by Molecular Profiling," *Cancer Res.* 62:6278-6288.
West et al. (Jun. 2005) "Determination of Stromal Signatures in Breast Carcinoma," *PLpS Biol.* 3(6):e187-.
White et al. (Jul. 1987) "An Evaluation of Confocal Versus Conventional Imaging of Biological Structures by Fluorescence Light Microscopy," *J. Cell Biol.* 105(1):41-48.
White et al. (Aug. 1004) "Targeted Disruption of Beta 1-Integrin in a Transgenic Mouse Model of Human Breast Cancer Reveals an Essential Role in Mammary Tumor Induction," *Cancer Cell* 6:159-170.
Williams et al. (Feb. 2005) "Interpreting Second-Harmonic Generation Images of Collagen I Fibrils," *Biophys. J.* 88:1377-1386.
Wokosin et al. (Jan. 2003) "Optical Workstation with Concurrent, Independent Multiphoton Imaging and Experimental Laser Microbeam Capabilities," *Rev. Sci. Instrum.* 74(1):193-201.
Wolbarst et al. (Jan. 2006) "Evolving and Experimental Technologies in Medical Imaging," *Radiology* 238(1):16-39.
Wolf et al. (2005) "Functional Imaging of Pericellular Proteolysis in Cancer Cell Invasion," *Biochimie.* 87(3-4):315-320.
Wolf et al. (Jan. 20, 2003) "Compensation Mechanism in Tumor Cell Migration: Mesenchymal-Amoeboid Transition after Blocking or Pericellular Proteolysis," *J. Cell. Biol.* 160:267-277.
Wozniak et al. (Jan. 2005) "R-Ras Controls Membrane Protrusion and Cell Migration Through the Spatial Regulation of Rac and Rho," *Mol. Biol. Cell* 16(1):84-96.
Wozniak et al. (Nov. 10, 2003) "ROCK-Generated Contractility Regulates Breast Epithelial Cell Differentiation in Response to the Physical Properties of a Three-Dimensional Collagen Matrix," *J. Cell. Biol.* 163:583-595.
Yazdanfar et al. (Jun. 14, 2004) "Interferometric Second Harmonic Generation Microscopy," *Optic. Exp.* 12(12):2739-2745.
Zhang et al. (Dec. 2002) "Creating New Fluorescent Probes for Cell Biology," *Nat. Rev. Mol. Cell Biol.* 3(12):906-918.
Zipfel et al. (Nov. 2003) "Nonlinear Magic: Multiphoton Microscopy in the Biosciences," *Nat. Biotechnol.* 21:1369-1377.
Zipfel et al. (Jun. 10, 2003) "Live Tissue Intrinsic Emission Microscopy Using Multi-Photon-Excited Native Fluorescence and Second Harmonic Generation," *Proc. Nat. Acad. Sci. USA* 100:1075-7080.
Zoumi et al. (Aug. 20, 2002) "Imaging Cells and Extracellular Matrix in Vivo by Using Second-Harmonic Generation and Two-Photon Excited Fluorescence," *Proc. Nat. Acad. Sci. USA* 99:11014-11019.
International Search Report, Corresponding to International Application No. PCT/US08/55453, Mailed Aug. 15, 2008.
Written Opinion, Corresponding to International Application No. PCT/US/08/55453, Mailed Aug. 15, 2008.

\* cited by examiner

I. Providing a test tissue sample from a test subject.

Optionally: The test tissue sample comprises:
1. A mammary tissue component.
2. An tumor component, such as an epithelial tumor component.
3. A stromal or epithelial component.

↓

II. Generating a test image or test imaging data from the test tissue sample including using a nonlinear optical imaging technique (e.g., MPM, FLIM, SLIM, and/or SHG techniques)

Optionally: The test image or test imaging data and comprises:
1. One or more FAD fluorescence intensity images.
2. One or more FAD fluorescence lifetime images.
3. One or more FLIM or SLIM images having a FAD fluorescence component.

↓

III. Analyzing the test image or test imaging data of the test tissue sample by measuring: (i) Fluorescence intensities,
(iii) Fluorescence lifetime values or both of fluorescence from endogenous FAD in said test tissue sample.

↓

IV. Comparing the test image or test imaging data with a reference image or reference imaging data corresponding to one or more reference tissues.

Optionally: Further carrying out one or more steps of:
1. Determining the percentage differences between at least a portion of said fluorescence intensities of said endogenous FAD in said test tissue sample and a reference fluorescence value or set of reference fluorescence values.
2. Fitting temporal profiles of FAD fluorescence in said test tissue sample to the expression and determining $\tau_1$, $\tau_2$, $\tau_m$:

$$I_f(t) = \sum_{i=0}^{n} a_i \exp^{(-t/\tau_i)} + c = a_1 \exp^{-t/\tau_1} + a_2 \exp^{-t/\tau_2} + a_3 \exp^{-t/\tau_3} + \ldots + c$$

3. Determining the percentage difference of the a first component of the fluorescent lifetime ($\tau_1$), a second component of the fluorescent lifetime ($\tau_2$) or a weighted mean values ($\tau_m$) of the fluorescent lifetime with a reference fluorescence lifetime value or set of reference fluorescence lifetime value values.

Figure 1

USE OF ENDOGENOUS FLUORESCENCE TO IDENTIFY INVADING METASTATIC BREAST TUMOR CELLS

CROSS-REFERENCE TO RELATED APPLICATIONS

This application claims priority under 35 U.S.C. 119(e) to U.S. Provisional Patent Application 60/892,687 filed Mar. 2, 2007, which is hereby incorporated by reference in its entirety.

STATEMENT REGARDING FEDERALLY SPONSORED RESEARCH OR DEVELOPMENT

This invention was made with United States government support awarded by the following agencies: NIH grants CA076537 and EB000184. The United States government has certain rights in the invention.

BACKGROUND OF INVENTION

Biomedical imaging plays a central role in a large number of diagnostic and therapeutic procedures including visualizing external and internal anatomical and physiological structures, features, and systems; evaluating complex biological events in the body at the organ, tissue, cellular, and molecular levels, and facilitating image guided surgery techniques. Imaging allows physicians and other health care professionals to detect and diagnose the onset of disease, injury, and other disorders at an early stage and to accurately monitor progression or remission of a condition. Biomedical imaging also enables delivery of targeted and minimally invasive therapies for treating and managing a range of conditions. A large number of applications of biomedical imaging have matured into robust, widely used clinical techniques including planar projection and tomographic x-ray imaging, magnetic resonance imaging, ultrasound imaging, and gamma ray imaging.

Biomedical images are generated by detecting electromagnetic radiation, nuclear radiation, acoustic waves, electrical fields, and/or magnetic fields transmitted, emitted and/or scattered by materials, where the materials can be biological materials and/or materials introduced in the body such as implants, contrast agents, infusions, tracers, etc. Modulation of energy (e.g., radiative, acoustic, etc.) and/or particles provided to a sample via interaction with materials such as biological molecules and tissue structures yields patterns of transmitted, scattered or emitted radiation acoustic waves, electrical fields or magnetic fields that contain useful anatomical, physiological, and/or biochemical information. Modulation may occur via mechanisms involving interactions of endogenous materials in the sample and/or mechanisms involving interactions of exogenous imaging agents introduced to a sample to enhance the usefulness of the acquired image, such as contrast agents, dyes, optically or radiolabel materials, biomarkers, and other agents. Biomedical imaging has been demonstrated as generally useful for providing images of surface and subsurface components of tissue samples and also provides a means of real time monitoring of components of biological samples, in vivo and in vitro.

Advanced optical imaging methods, such as confocal scanning laser tomography and optical coherence tomography, have emerged as valuable molecular imaging techniques for visualizing biological processes at a cellular and subcellular (e.g., molecular) levels. Established optical molecular imaging techniques are based on monitoring spatial variations in a variety of optical parameters including the intensities, polarization states, and frequencies of transmitted, reflected, and emitted electromagnetic radiation. Given that many biological materials of interest are highly turbid with respect to most frequencies in the ultraviolet and visible regions of the electromagnetic spectrum, research is currently directed to developing and enhancing imaging techniques using near infrared excitation radiation from about 700 nanometers to about 1200 nanometers corresponding to an "optical window" present in many of these materials. Electromagnetic radiation of this wavelength range is capable of substantial penetration (e.g., up to a millimeter) in many biological materials and is considerably less phototoxic than visible and ultraviolet electromagnetic radiation. Infrared optical molecular imaging techniques, therefore, offer the promise of providing nondestructive and noninvasive imaging of subsurface biological structures in biological samples.

Recent advances in high intensity, mode locked near infrared laser optical sources make nonlinear optical imaging methods, such as multiphoton (MP) microscopy and second harmonic generation (SHG), an important class of infrared molecular imaging methods for visualizing cellular and subcellular structures in biological samples. Nonlinear imaging techniques are particularly useful for providing high resolution images for probing physiology, morphology, cellular microenvironments, and cell-extracellular matrix and cell-cell interactions in intact tissues and living organisms. MP microscopy uses a high intensity, temporally short laser pulse to provide highly localized nonlinear excitation of fluorescence. In two photon fluorescence excitation techniques, for example, absorption of two lower energy photons simultaneously excites an electronic transition in a fluorophor, thereby causing radiative decay resulting in fluorescence emission of a single higher energy photon. As the probability of two photon absorption is relatively low (for example, as compared to single photon absorption), excitation in this technique is limited to a spatially confined focused region of the excitation beam having a sufficiently high intensity of photons. Second harmonic generation, in contrast, does not arise from an absorptive process. Rather, the second harmonic phenomenon results from a nonlinear scattering interaction of radiation with a non-centrosymmetric environment of a sample. In this technique, an intense laser field is provided to the sample that induces a nonlinear, second order, polarization in the spatial orientation of molecules exposed to the excitation radiation. The induced polarization results in generation of a coherent wave having a frequency that is exactly two times that of the incident excitation radiation. In both MP microscopy and SHG, a two dimensional image is typically generated by detecting fluorescence or polarized light, respectively, while the excitation beam is systematically scanned across a given layer of the sample. Three dimensional images are formed by scanning a plurality of layers at different depths.

A number of advantages are provided by nonlinear techniques relative to conventional linear optical imaging techniques. First, these techniques are ideally suited for use of infrared excitation radiation, particularly having wavelengths in the optical window region from about 700 nanometers to about 1200 nanometers of many biological samples. Thus, nonlinear optical techniques are capable of penetrating and imaging many types of tissues and typically do not lead to significant photoinduced sample degradation during analysis. Second, nonlinear optical imaging methods are capable of providing images with enhanced axial resolution relative to conventional optical imaging techniques due to the highly localized excitation arising from the nonlinear dependence of excitation rate on illumination intensity. Third, some applications of nonlinear advanced optical techniques to biomedical imaging, such as second harmonic generation methods, do not require exogenous labeling/staining. These techniques, therefore, can eliminate the need for complex and invasive labeling procedures common to conventional optical molecular imaging methods. Finally, different nonlinear techniques may be combined and used in tandem to provide complementary information relating to tissue structure and composition. For example, the combination of MP and SHG images provides enhanced cellular and subcellular information, as each technique employs fundamentally different excitation processes and, thus, provides substantially different contrast mechanisms.

Given the demonstrated capabilities of nonlinear optical imaging techniques for probing cellular and subcellular morphology and composition, researchers are currently pursuing applications of these techniques for detecting, diagnosing, and monitoring the onset and progression of disease. Proposed applications of nonlinear optical imaging include diagnosis of cancer and in situ evaluation of angiogenesis and metastasis processes, and monitoring the progression of neurodegenerative diseases such as Alzheimer's disease. Although the potential for such applications, including endoscopy and optical biopsy applications, is clear, these techniques have not yet matured to the point so as to provide a robust clinical tool. To develop this, and other important applications of nonlinear optical imaging, histopathological features and structural motifs in biomedical images that correlate with specific disease conditions in human and animal patients must be identified and characterized, particularly as a function of the progression or remission of a disease. Further, enhancements are also need to transform the instrumentation used in nonlinear imaging techniques into a reliable instrument capable of implementation in range of clinical applications.

SUMMARY OF THE INVENTION

The present invention broadly provides methods and systems for detecting, identifying, and characterizing conditions in humans and in other animal subjects, including diseases and other disorders, by analyzing fluorescence from endogenous flavin adenine dinucleotide (FAD) fluorophors present in biological materials and samples. In particular embodiments, the invention relates to conditions of the human breast including cancers such as carcinoma. Methods and systems are provided for detecting, locating, and characterizing tumors, particularly epithelial tumors, via nonlinear optical imaging techniques capable of accurately characterizing fluorescence intensities and fluorescent lifetime parameters from endogenous FAD fluorophors present in a test tissue sample. Nonlinear optical imaging techniques beneficial in the present invention include multiphoton microscopy (MPM), multiphoton fluorescent lifetime imaging microscopy (FLIM), harmonic generation microscopy, and spectral lifetime imaging microscopy (SLIM) techniques providing high resolution multi dimensional imaging (including two-dimensional and three-dimensional) of test tissue samples. The methods and systems support versatile implementation including providing in vivo analysis (including application to a patient sample in situ over real time), and in vitro analysis (including ex vivo as analogous to classical histopathology) of test tissue samples. Methods of the present invention have applications for clinical pathology, optical biopsy and endoscopy. In some embodiments, for example, the present methods analyze the fluorescent properties of endogenous FAD biomarkers in biological materials and samples to identify and characterize invading metastatic breast tumor cells.

The present invention further and preferably for some applications provides noninvasive and nondestructive methods and systems that are capable of identifying and characterizing cancer in non-fixed, non-sectioned, and/or non-stained tissue, including excised tissue samples and tissues in whole organisms. The present invention provides highly sensitive, selective and specific methods that are capable of directly evaluating subsurface tumor development and progression over the spectrum from a normal state to advanced cancer states, including invasive and metastatic states. The present methods and systems are capable of detecting and characterizing (e.g., classifying, staging etc.) cancer in a range of tissue types, including breast tissue and epithelial tissue. In some specific applications, for example, the present methods are utilized to support clinical diagnosis and treatment in connection with epithelial tumor development, progression, local invasion and metastasis. Systems and methods of the present invention provide diagnostic information that is different from, and can be complementary to, information provided by other diagnostic platforms, such as mammography, ultrasound and conventional histological staining techniques. Methods of the present invention can be carried out rapidly, in real time and, therefore, are useful tools to support biopsy, surgical resection and other clinical diagnostic and treatment procedures for cancer.

In one aspect, the invention provides a method of evaluating a test tissue sample for the diagnosis of cancer. A method of this aspect comprises the steps of: (i) providing the test tissue sample from a test subject, wherein the test tissue sample comprises a mammary tissue component; (ii) generating a test image or test imaging data from the test tissue sample using a nonlinear optical imaging technique; and (iii) analyzing the test image or test imaging data of the test tissue sample by measuring fluorescence intensities, fluorescence lifetime values or both of fluorescence from FAD in the test tissue sample, thereby evaluating the test tissue sample for the diagnosis of cancer. In an embodiment, the test tissue sample is a breast tissue sample and/or the test tissue sample is intact and non-fixed. Evaluation of fluorescence information from FAD in the present techniques is beneficial because it is an endogenous fluorophor in a range of important tissues from humans and other species and is present at concentrations allowing for effective multiphoton fluorescence characterization. Further, use of an endogenous fluorophor in the present methods eliminates the need for providing imaging agents to the sample, such as optical contrast agents or fluorescent probes, thereby enabling sensitive optical evaluation without requiring a change in the composition of the test tissue sample.

In an embodiment, test image or test image data is generated comprising a FAD fluorescence image of a layer or plurality of layers of the test tissue sample. Useful FAD fluorescence images for the present methods include fluorescence intensity images of the test tissue sample and fluorescence lifetime images of the test tissue sample. Preferably for some embodiments, a fluorescence intensity image and one or more fluorescence lifetime images are generated, such as a plurality of fluorescence lifetime images corresponding to fluorescence from the test sample having different wavelengths, for example as generated using spectral lifetime imaging techniques. Nonlinear microscopy techniques for generating FAD fluorescence images useful in the present methods include one or more of those selected from the group consisting of multiphoton microscopy (MPM), multiphoton fluorescent lifetime imaging microscopy (FLIM), and spectral lifetime imaging microscopy (SLIM). Methods of this aspect of the present invention may further comprise the step of generating additional images of the test tissue, including images corresponding to different layers or regions of the test tissue and images generated by different linear and/or non-linear optical imaging techniques. Optionally, methods of this embodiment include the step of comparing and/or combining different images of the test tissue for the detection and/or characterization of fluorescence from endogenous FAD in test tissue.

In the context of this description, the expression "fluorescence intensity image" refers to a two-dimensional or three-dimensional distribution of fluorescence intensity measurements, or parameters derived from fluorescence intensity measurements, wherein spatial information relating to the positions of fluorophors in the test tissue sample or a layer or plurality of layers of the test tissue sample is retained in the image. In some embodiments, for example, the positions of intensity values in a distribution of fluorescent intensity measurements comprising a fluorescence intensity image correlate at least in part to the relative positions of the fluorophors in the test tissue sample. In the context of this description, the expression "fluorescence lifetime" refers to a temporal characteristic of fluorescence from a fluorophor. Fluorescence lifetime may be characterized by the functional dependence of the fluorescence intensity observed upon excitation (e.g., pulsed excitation). Useful parameters for characterizing fluorescence lifetime include an exponential function or series of exponential functions having a primary component (e.g., $\tau_1$) and one or more higher components (e.g., $\tau_2, \tau_3, \tau_4, \ldots \tau_x$) as described in the following expression:

$$I_f(t) = \sum_{i=0}^{n} a_i \exp^{(-t/\tau_i)} + c = a_1 \exp^{-t/\tau_1} + a_2 \exp^{-t/\tau_2} + a_3 \exp^{-t/\tau_3} + \ldots + c \quad (I)$$

wherein $I_f(t)$ is the fluorescence intensity as a function of time, t is time, $\tau_1$ is a primary component of the fluorescence lifetime, $\tau_2, \tau_3 \ldots \tau_x$ are higher components of the fluorescence lifetime, $a_1, a_2 \ldots a_x$ are each constants independent of each other, and c is a constant. The expression, "fluorescence lifetime image" refers to a two-dimensional or three-dimensional distribution of fluorescence lifetime measurements, or parameters derived from measurements of the temporal fluorescence lifetimes, wherein spatial information relating to the positions of fluorophors in the test tissue sample or a layer or plurality of layers of the test tissue sample is retained in the image. In some embodiments, for example, the positions of fluorescence lifetime measurements in a distribution of fluorescence lifetime measurements comprising a fluorescence lifetime image correlate, at least in part, to the relative positions of the fluorophors in the test tissue sample.

Optionally, methods of this diagnostic aspect of the present invention may further comprise the step of analyzing the test image or test imaging data of the test tissue sample by comparison with one or more reference images or reference imaging data corresponding to one or more reference tissues. In some embodiments, for example, the analyzing step further comprises one or more comparison steps selected from the group consisting of: (i) comparing at least a portion of the fluorescence intensities to a reference fluorescence intensity value or set of reference fluorescence intensity values corresponding to fluorescence from endogenous FAD in one or more reference tissues; and (ii) comparing at least a portion of the fluorescence lifetime values to a reference fluorescence lifetime value or set of reference fluorescence lifetime values corresponding to fluorescence from endogenous FAD in the one or more reference tissues. Comparison steps in certain aspects of the present invention are useful for identifying and characterizing intensities in a FAD fluorescence intensity image or fluorescence lifetime measurements in a FAD fluorescence lifetime image that can be quantitatively correlated using the present methods generally with the stage or progression of cancer, and specifically with metastatic potential and the presence of invading metastatic tumor cells. In embodiments, further correlations are developed for association of certain FAD fluorescence intensities or FAD fluorescence lifetimes in a test image with clinical terminology including "benign" and "malignant." In embodiments, FAD fluorescence intensities or FAD fluorescence lifetimes in fluorescence intensity and/or fluorescence lifetime images acquired over a period of time are further used in the context of informing a diagnostic assessment such as by noting the qualitative and/or quantitative changes and/or rates of change in onset, progression or remission of cancer. Therefore, the methods of the present invention enable the use of measurements and analysis of FAD fluorescence intensities or FAD fluorescence lifetimes in certain diagnostic applications of the present invention for assessing the presence or absence of invasion, metastasis and/or metastatic potential.

Methods of some embodiments may further include the step of identifying patterns of fluorescence intensities or fluorescence lifetime measurements in test FAD fluorescence intensity and fluorescence lifetime images that are correlated by the present invention with the presence, onset, staging and progression of cancer. In the context of this description, patterns of the present methods include those comprising a plurality of intensities or fluorescence lifetime measurements having values that differ from a reference value or series of reference values derived from FAD fluorescence images acquired from reference tissue. In other embodiments, patterns of the present methods include those comprising a plurality of FAD intensities or fluorescence lifetime measurements that have values relative to each other indicative of presence, absence and stage of cancer in a test sample.

A variety of reference images, reference data and reference tissues are useful in methods of the present invention. In an embodiment, FAD fluorescence intensity and/or fluorescence lifetime reference values can each independently relate to a reference tissue having a normal condition (i.e., noncancerous) or a disease condition at a particular disease stage or historical time point. For example, FAD fluorescence intensity and/or FAD fluorescence lifetime reference values can be a previously assessed value from the same or different test sample from the same patient or a different patient. When reference values are derived from the same patient, there can be a particular diagnostic advantage in such values serving as an internal control, whether or not temporally synchronized with the test tissue sample. In the specific example where historical reference values reflect a disease state, the reference values can serve to evaluate the present test tissue sample while also providing other information, e.g., regarding the level or rate of change. When the reference values reflect a disease state, there can be a diagnostic advantage in facilitating a comparison of the reference image with the test image to accurately assess the test sample. In a preferred embodiment, greater diagnostic information is achieved by accruing and evaluating multiple reference values corresponding to a plurality of FAD fluorescence references images (e.g., FAD fluorescence intensity or lifetime images) and/or reference image data.

In some embodiments, for example, a reference fluorescence intensity value or set of reference fluorescence intensity values, and/or a reference fluorescence lifetime value or set of reference fluorescence lifetime values are determined from one or more reference tissues having a normal condition or alternatively one or more reference tissues having a disease condition. In an embodiment, the test tissue sample provides one or more first stromal or epithelial regions suspected of a cancerous condition; wherein the test tissue sample also serves as the reference tissue, wherein the reference fluorescence intensity value or set of reference fluorescence intensity fluorescence intensity values, the reference fluorescence lifetime value or set of reference fluorescence lifetime values or both are determined from one or more second stromal or epithelial regions of the test sample having a normal condition. In an embodiment, the test tissue sample provides one or more stromal or epithelial regions suspected of a cancerous condition; wherein the test tissue sample also serves as the reference tissue, wherein the reference fluorescence intensity value or set of reference fluorescence intensity values, the fluorescence lifetime values or set of reference fluorescence lifetime values or both are determined from one or more tumor regions of the test sample. In an embodiment, the test tissue sample provides one or more first tumor regions suspected of an invasive state; wherein the test tissue sample also serves as the reference tissue, wherein the reference fluorescence intensity value or set of reference fluorescence intensity values, the reference fluorescence lifetime values or set of reference fluorescence lifetime values or both are determined from one or more second tumor regions having a noninvasive state such as a primary tumor.

In some applications, the difference between intensities of endogenous FAD fluorescence in the test tissue sample and reference FAD fluorescence value or set of reference values are determined and evaluated. In an embodiment useful for characterizing cancer and/or tumor cells present in test tissue, the present methods further comprises the steps of: (i) determining the percentage difference between at least a portion of the fluorescence intensities of the endogenous FAD in the test tissue sample and a reference FAD fluorescence value or set of reference FAD fluorescence values; and (ii) identifying the presence of invasive and/or metastatic cells in the test tissue upon observing a percentage difference (Intensity Difference) between at least a portion of the fluorescence intensities and the reference fluorescence intensity value or set of reference values greater than or equal to 50%. In an embodiment, the percent difference between an individual fluorescence intensity value ($I_{Test}$) in a test image and a reference fluorescence intensity value ($I_{ref}$) is defined using the following expression:

$$\text{Intensity Difference} = \frac{(I_{Test} - I_{Ref})}{I_{Ref}} \times 100\% \qquad (II)$$

Optionally, the present methods include the step of generating an image of intensity difference values. In some embodiments, for example, observation of fluorescence intensities for FAD proximate to and/or within a tumor mass in the test tissue having values larger than fluorescence intensities of FAD corresponding to the primary tumor mass in the test tissue or other reference tissue provides an indication of presence, stage and or extent of invasive cells. In some embodiments, for example, observation of fluorescence intensities of FAD proximate to and/or within a tumor mass in the test tissue having values different than fluorescence intensities of FAD corresponding to stromal or epithelial cells in the test tissue or other reference tissue provides an indication of presence, stage and or extent of invasive cells. In some embodiments, for example, this difference is used to identify the sub-population of invasive cells relative to non-invasive cells in the primary tumor mass; or relative to normal epithelial cells or stromal cells (i.e. fibroblasts, immune cells, etc.).

In an embodiment useful for characterizing cancer and/or tumor cells present in test tissue, temporal profiles of FAD fluorescence in the test tissue sample are fit to Equation I, as defined above, and a primary lifetime component ($\tau_1$), and/or higher lifetime components (e.g., $\tau_2, \tau_3 \ldots \tau_x$) are determined, and optionally used to generate a fluorescence lifetime image of the test tissue sample. Optionally, the weighted mean values lifetime component ($\tau_m$) is determined using the determined primary and higher lifetime component values, for example using the expression:

$$\tau_m = \frac{(w_1\tau_1 + w_2\tau_2 + w_3\tau_3 \ldots w_x\tau_x)}{(w_1 + w_2 + w_3 \ldots w_x)} \qquad (III)$$

Wherein $w_1, w_2, w_3, \ldots w_x$. are weight factors, and optionally used to generate a fluorescence lifetime image of the test tissue sample. In an embodiment, the weight factors in Equation III are calculated based on the best fit.

The first component ($\tau_1$) of the fluorescent lifetime of the endogenous FAD in the test tissue sample; the second component ($\tau_2$) of the fluorescent lifetime of the endogenous FAD in the test tissue sample; and/or the weighted mean values ($\tau_m$) of the fluorescent lifetime of the endogenous FAD in the test tissue sample are evaluated by comparison with one or more reference fluorescence lifetime values derived from reference tissue. In an embodiment certain methods further comprise the steps of (i) determining the percentage deviations between at least a portion of the first components ($\tau_1$), second components ($\tau_2$) or weighted mean values ($\tau_m$) and the reference fluorescence lifetime value or set of reference lifetime values; and (ii) identifying the presence of invasive or metastatic cells in the test tissue upon observing a percentage difference (Lifetime Difference) between the first components ($\tau_1$), second components ($\tau_2$) and/or weighted mean values ($\tau_m$) and the reference fluorescence lifetime value or set of reference fluorescence lifetime values greater than or equal to 40% for $\tau_1$, 10% for 2, and/or 50% for $\tau_m$. The present methods may use lifetime differences of any one of $\tau_1, \tau_2, \tau_x$, and $\tau_m$, or any combinations of these parameters.

In an embodiment, the percent difference between a fluorescence lifetime value (e.g., $\tau_1, \tau_2, \tau_m$, etc.) in a test image and a reference fluorescence lifetime value ($\tau_{ref}$) is defined using the following expression:

$$\text{Lifetime Difference} = \frac{(\tau_{Test} - \tau_{Ref})}{\tau_{Ref}} \times 100\% \qquad (IV)$$

wherein $\tau_{Test}$ can be any one of $\tau_1, \tau_2, \tau_x, \tau_m$, etc. for individual FAD lifetime measurements and wherein $\tau_{ref}$ can be any one of $\tau_1, \tau_2, \tau_m$, etc. for reference lifetime values for a reference tissue. In some embodiments, for example, observation of second components ($\tau_2$) and weighted mean values ($\tau_m$) of the fluorescent lifetime of endogenous FAD in the test tissue sample proximate to and/or within a tumor mass in the test tissue sample having values larger than of second components ($\tau_2$) and weighted mean values ($\tau_m$) of the fluorescent lifetime of endogenous FAD corresponding to the primary tumor mass in the test tissue or other reference tissue provides an indication of presence, stage and or extent of invasive cells. In some embodiments, for example, observation of second components ($\tau_2$) and weighted mean values ($\tau_m$) of FAD proximate to and/or within a tumor mass in the test tissue having values different than the second components ($\tau_2$) and weighted mean values ($\tau_m$) of fluorescence lifetimes corresponding to FAD associate with stromal or epithelial cells in the test tissue or other reference tissue provides an indication of presence, stage and/or extent of invasive cells. In some embodiments, for example, this difference is used to identify the sub-population of invasive cells relative to non-invasive cells in the primary tumor mass; or relative to normal epithelial cells or stromal cells (i.e. fibroblasts, immune cells, etc.). Optionally, the methods of the present invention include the step of generating an image of lifetime difference values determined by the present methods.

Test images and test image data is generated in the present invention by exciting endogenous FAD fluorophors and measuring the resulting fluorescence from FAD fluorophors in a test tissue sample. Imaging techniques employing multiphoton excitation allow the use of electromagnetic radiation in the visible or near infrared radiation regions of the spectrum for excitation that effectively penetrates many test tissue samples without resulting in photoinduced degradation or other unwanted changes of composition. In an embodiment, for example, selective imaging of endogenous FAD is achieved by multiphoton excitation using electromagnetic radiation having wavelengths selected over the range of 860 nm to 940 nm, preferably for some applications 890 nanometers, or the 2-photon cross section surrounding the excitation maximum of 450 nm for FAD, and detection of fluorescence having wavelengths selected over the range of 510 nm to 550 nm, preferably for some applications 530 nanometers. Multiphoton excitation also provides the benefit of accessing superior image resolution in fluorescence intensity and fluorescence lifetime images relative to conventional fluorescence excitation techniques.

Optionally, specific methods of the present invention further comprise the step of generating one or more harmonic generation image(s) of the test tissue sample using harmonic generation microscopy (e.g., second harmonic generation, third harmonic generation, fourth harmonic generation etc.). In some embodiments, for example, harmonic generation microscopy is used to generate a harmonic generation image showing the distribution and structure of stromal collagen in the test tissue sample. Such harmonic generation images provide complementary diagnostic information for the evaluation of cancer in test tissue samples in some of the present methods.

In another aspect, the invention provides a method of diagnosing breast cancer that is complementary to conventional breast cancer screening and/or diagnostic techniques. In an embodiment, methods of the present invention allow improved identification and characterization of invasive tumor cells and cells exhibiting metastatic potential. In an embodiment, methods of the present invention allow improved characterization of metastatic potential in cancerous tissue, including epithelial tumors.

In some embodiments, FAD fluorescence intensity images and/or FAD fluorescence lifetime images are analyzed using statistical and or advanced signal processing techniques. FAD fluorescence Images and/or image date is analyzed in some methods using statistical and or advanced signal processing techniques capable of generated quantitative parameters that can be correlated to the presence or absence of disease, and/or the stage or identity of a disease, and/or potential clinical outcomes. In specific embodiments of the present invention, analysis of FAD fluorescence intensity and fluorescence lifetime images may be carried out by a doctor, other healthcare professional, researcher, a computer or computer processor, or any combination of these. In one embodiment providing a partially or fully automated method, analysis of FAD fluorescence intensity and fluorescence lifetime images is carried out via a computer-based technique. While it is preferred for some specific applications of the present invention that a computer be used to accomplish all the steps of the present methods with final clinical staff oversight, it is contemplated that a computer may be used to perform only a certain step or selected series of steps in the present methods. The present invention includes partial and fully automated methods for evaluating and diagnosing cancer in tissues.

Methods of this aspect of the present invention are useful for identifying the presence, absence or invasiveness of cancer and/or for assessing the composition, state, physical dimensions, or progression of tumors and invasive tumor components in a sample. In one embodiment of this aspect of the present invention, a test tissue sample from a test subject is provided that comprises a stromal or epithelial component. Examples of particularly useful tissues for evaluation by the present methods include breast, cervix, lung, prostate, esophagus, colon, skin, eye, and other tissues. In embodiments, tissue/cell components of epithelial, stromal, mesenchymal, neuronal, immune, vascular origin and certain extracellular matrix components are apt for examination using the present methods and systems.

In another specific aspect, the invention provides a method for evaluating a tumor in a tissue sample for invasiveness or metastatic potential comprising the steps: (i) obtaining a plurality of test images from said tissue sample using one or more nonlinear optical imaging techniques; said test images comprising a multiphoton intensity image of said test sample and a fluorescence lifetime image of said test sample; (ii) analyzing said multiphoton intensity image by measuring fluorescence intensities of endogenous FAD in said test tissue sample; (iii) analyzing said fluorescence lifetime image by measuring fluorescent lifetime values from endogenous FAD in said test tissue sample; and (iv) comparing said fluorescence intensities and fluorescent lifetime values to a set of reference values corresponding to endogenous FAD in said one or more reference tissues; thereby evaluating a tumor for invasiveness or metastatic potential. In an embodiment of this aspect, the tumor is an epithelial tumor.

In another specific aspect, the invention provides a method of locating a tissue region associated with a cancer risk comprising the steps of: (i) providing a test tissue sample, (ii) generating a test image or test imaging data from the test tissue sample using a nonlinear optical imaging technique, (iii) analyzing said test image or test imaging data of the test tissue sample by measuring fluorescence intensities, fluorescent lifetime values or both from endogenous FAD in said test tissue sample; (iv) comparing at least a portion of said fluorescence intensities or fluorescent lifetime values to a reference value or set of reference values corresponding to endogenous FAD in said one or more reference tissues; and (v) identifying fluorescence intensities or fluorescent lifetime values different from said reference value or set of reference values, and spatially orienting said fluorescence intensities or fluorescent lifetime values that are different from said reference value or set of reference values with respect to the corresponding tissue sample or a three-dimensional representation of the tissue sample; thereby locating said tissue region associated with said cancer risk. In an embodiment of this aspect, the tissue region associated with said cancer risk is a region containing invading metastatic tumor cells.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

FIG. 1. provides a schematic diagram illustrating a method of the present invention for evaluating a test tissue for the identification, diagnosis and treatment of cancer, for example breast cancer.

Figure 5A:
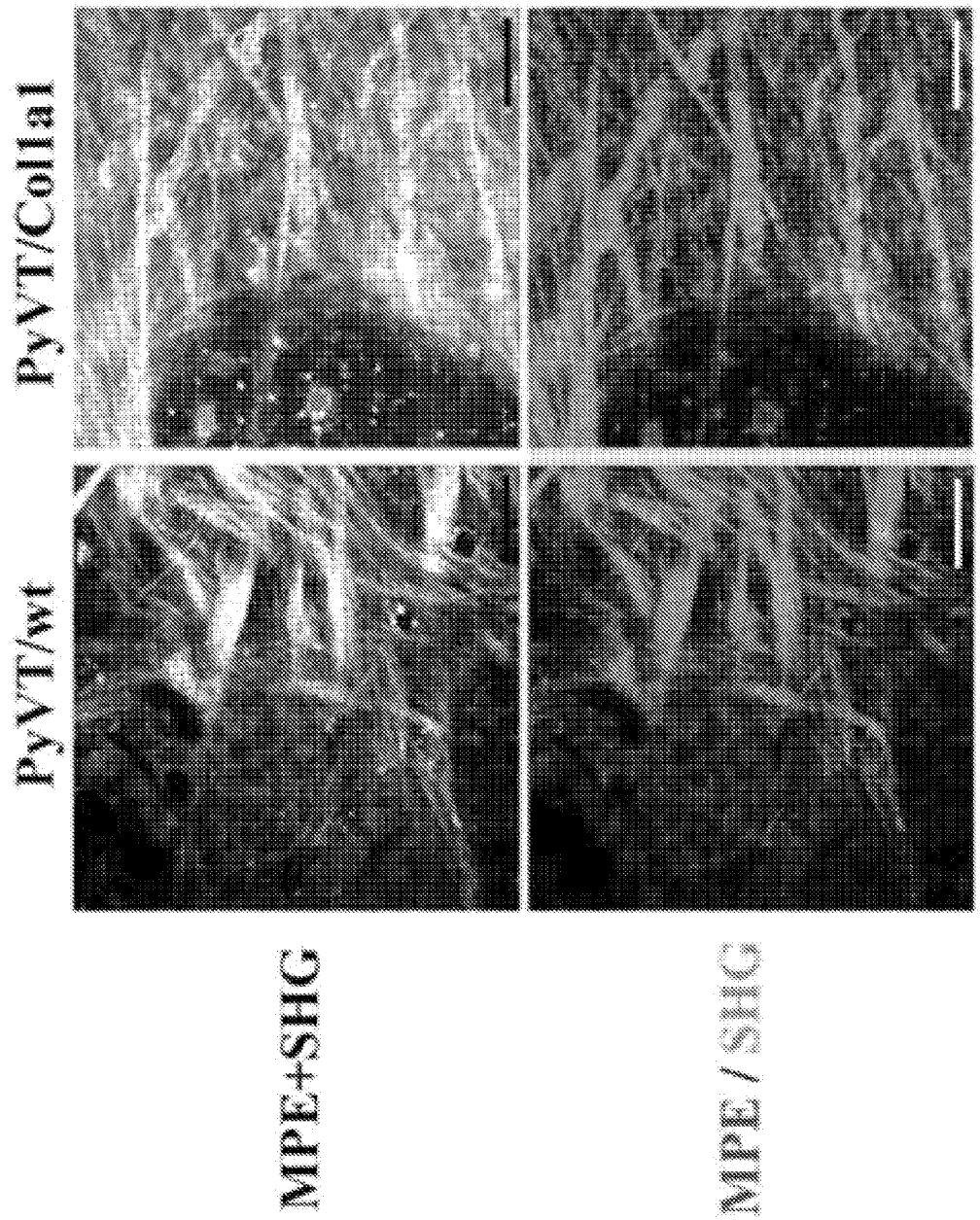

FIG. 5. Increased Metastasis Associated with Dense Stromal Collagen. (a) Combined and signal separated MPE/SHG images of late stage (15 week) invasive PyVT/wt and PyVT/Col1a1 tumors. Note that tumors arising in either wt or Col1a1 backgrounds are invasive at 15 weeks and display significant regions of TACS-3. Scale bars=25 µm. (b) Increased lung metastasis at 15 weeks in mice that formed tumors in collagen-dense mammary glands (PyVT/Col1a1) when compared to mice that formed tumors in control glands (PyVT/wt). (c) Tumor cells extracted from collagen dense tumors (PyVT/Col1a1) showed increased migration when compared to tumor cells from control tumors (PyVT/wt) as measured by transwell migration assays with serum as the chemotractant. *Indicates a statistically significant ($p<0.05$) following analysis with paired t-tests.

Figure 6:
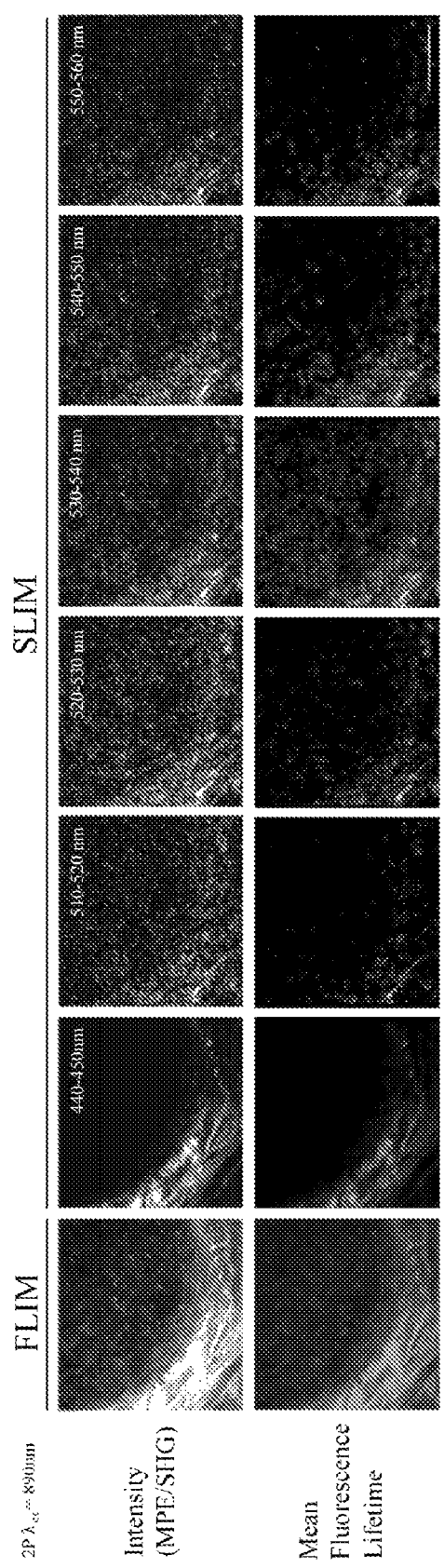

FIG. 6. Multiphoton Spectral Lifetime Imaging Microscopy (SLIM) Analysis of Live Tumors. Multiphoton fluorescence lifetime imaging microscopy (FLIM) demonstrates the measurable fluorescence lifetimes of live tumor cells as already shown. Using SLIM, the fluorescence lifetimes following 890 nm two-photon excitation of live 3D tumors are measured within a defined spectra, allowing identification of the emitting fluorophore and noise removal from adjacent spectra. For instance, examination of the 440-450 nm emission spectra from SLIM confirms the presence of collagen bounding tumor cells. For an 890 nm two-photon excitation the SHG signal is maximal at 445 nm and has no lifetime (dark). Additionally, the maximal emission signal from tumor cells is 535 nm, indicating the emission results from excitation of the endogenous fluorophore FAD. Greyscale bar=0 to 1 ns.

DETAILED DESCRIPTION OF THE INVENTION

Referring to the drawings, like numerals indicate like elements and the same number appearing in more than one drawing refers to the same element. In general the terms and phrases used herein have their art-recognized meaning, which can be found by reference to standard texts, journal references and contexts known to those skilled in the art. The following definitions are provided to clarify their specific use in the context of the invention.

In the context of this description, the term "nonlinear" refers to photonic processes, such as fluorescence excitation or SHG scattering, that exhibit a rate that depends nonlinearly on the intensity of incident electromagnetic radiation. Nonlinear optical imaging methods useful in the present invention include, but are not limited to, MP microscopy (two photon excitation, three photon excitation, etc.), multiphoton fluorescent lifetime imaging microscopy (FLIM), spectral lifetime imaging microscopy (SLIM), and harmonic generation microscopy (second harmonic generation, third harmonic generation, fourth harmonic generation, etc.).

When used herein, the term "tissue sample" can refer to a portion of tissue from an animal subject. The sample can be intact and in situ, for example as part of a tissue or organ while remaining attached to the living animal. Alternatively, the sample can be an excised tissue portion which can optionally be further processed. In an embodiment, the excised sample is fixed. In an embodiment, the excised sample is stained, e.g., using conventional histopathology techniques. In an embodiment, the excised sample is frozen. In a particular embodiment, the sample is a mammalian breast tissue sample or epithelial tissue sample. In a preferred embodiment, the sample is a live or excised breast tissue portion which is structurally intact (e.g., unsectioned), unfixed, and unstained.

When used herein, the term "test tissue sample" generally refers to a tissue sample from a subject where a condition of the sample or the subject is unknown or suspected and it is desired to ascertain such condition. For example, a test tissue sample can be a breast sample from which a breast cancer diagnosis is to be determined. A tissue sample may be an excised tissue or a tissue that is part of an organism.

When used herein, the term "reference tissue sample" generally refers to a tissue sample for which a condition has been ascertained. For example, the reference could correspond to a sample having a known positive condition or a known negative condition, or a stage of a disease or normal physiological process, thus serving as a control or point of comparison in the evaluation of a different sample. A reference tissue sample may be an excised tissue or a tissue that is part of an organism.

When used herein, the term "reference value" indicates a value that has been assessed and serves as a point of comparison relative to a test fluorescence intensity or fluorescence lifetime value. For example, a reference value can be an amount or qualitative state as seen in a normal condition, a diseased condition, or as seen in a point along a continuum of conditions. Reference values include, but are not limited to, reference fluorescence values, reference fluorescence lifetime values, and values derived from these.

When used herein, the term "diagnosis" and other root word derivatives are as understood in the art and are further intended to include a general monitoring, characterizing and/or identifying a state of health or disease. The term is meant to encompass the concept of prognosis. For example, the diagnosis of breast cancer can include an initial determination and/or one or more subsequent assessments regardless of the outcome of a previous finding. The term does not necessarily imply a defined level of certainty regarding the prediction of a particular status or outcome.

When used herein, the term "cancerous" is as generally understood in the art. For example, the term can refer to a clinical condition of an unregulated or misregulated cell or tumor wherein there is an abnormal ability to proliferate, differentiate, and or migrate. The term is intended to address a variety of stages of disease progression. Thus the term precancerous is envisioned as encompassed within the conceptual scope whether viewed as a distinct earlier stage with a different potential and/or different level of disease significance relative to cancerous or viewed as part of a connected pathway or continuum. In a particular example, a cancerous condition can include having a prepalpable breast mass, wherein the mass is a tumor or suspected tumor.

When used herein, the term "intact" refers to material that has generally not been substantially disrupted. For example, the term can indicate a tissue sample that has not been sectioned.

When used herein, the term "in situ" refers to material that is in the natural or original position or place. For example, a breast tissue sample can be examined, relatively non-invasively, by imaging the sample while it remains in the breast.

When used herein, the term "excised" refers to material that has been removed from its natural location. For example, a breast tissue biopsy specimen is excised to facilitate its examination.

As used herein the following abbreviations apply: extracellular matrix (ECM); green fluorescent protein (GFP); multiphoton laser scanning microscopy (MPLSM); multiphoton excitation (MPE); fluorescence lifetime imaging microscopy (FLIM); second harmonic generation (SHG); nicotinamide adenine dinucleotide (NAD(P)H referred to here as NADH); and flavin adenine dinucleotide (FAD).

Human breast carcinoma cells frequently display changes in cellular metabolism that result in intrinsic autofluorescent signals. An aspect of the present invention takes advantage of the discovery that endogenous FAD fluorophors are useful biomarkers for evaluating cancer by identifying and characterizing tumors and other tissues, including breast tissue. Multiphoton microscopy (MPM), multiphoton fluorescence lifetime imaging microscopy (FLIM), and spectral lifetime imaging microscopy (SLIM) have been used to characterize the source of endogenous fluorescence from FAD biomarkers, thereby enabling its use for the evaluation of cancer in test tissue. For example, excitation at 890 nm in unfixed, unstained fresh mouse mammary tumors and subsequent SLIM analysis of fluorescence from tumors confirms the source of fluorescent emission used in the present methods is from endogenous FAD biomarkers. Analysis of changes in fluorescent intensity and lifetime components resulting from FAD fluorescence in test tissue are observed to increase in invading cells when compared to cells in the primary tumor mass. These measurable changes in endogenous fluorescent properties are used in the present methods to identify, characterize, and stage mammary tumors in animal models, human breast tumors and other test tissues.

Preferably for some embodiments, images comprising FAD fluorescence intensities and fluorescence lifetime values corresponding to test tissue are analyzed in real time to identify and assess the metastatic potential of invading cells in tumors. In this manner fluorescent intensities and fluorescent lifetime measurements from fluorescence of FAD within tumor cells are used to detect and stage human breast carcinoma. The methods of the present invention are especially useful for evaluating epithelial tumors which comprise nearly 90% of human tumors FIG. 1 provides a schematic diagram illustrating a method of the present invention for evaluating a test tissue for the identification, diagnosis and treatment of cancer, for example breast cancer. As shown in FIG. 1, a test tissue sample from a test subject is provided, which optionally comprises a mammary tissue component, a tumor component (e.g., a epithelial tumor component) and/or a stromal component. A test image or test image data is generated by exciting endogenous FAD present in the test tissue sample and observing fluorescence from FAD. Optionally, the test image comprises one or more fluorescence intensity images, fluorescence lifetime images, FLIM images and SLIM images. The test image or image data is analyzed by measuring fluorescence intensities and/or fluorescence lifetime values from fluorescence from endogenous FAD in the test tissue sample. In some embodiments, analysis of the test image or image data is carried out via comparison to one or more reference values from a reference tissue, such as one or more reference FAD fluorescence intensity values and/or one or more reference FAD fluorescence lifetime values. Comparison steps in the present invention optionally include the step of fitting temporal profiles of FAD fluorescence to Equation I, as provided above, and determining one or more parameters selected from the group consisting of a first component of the fluorescent lifetime ($\tau_1$), a second component of the fluorescent lifetime ($\tau_2$) or a weighted mean values ($\tau_m$) of the fluorescent lifetime. Useful reference values include reference fluorescence intensity values and reference fluorescence lifetime values acquired by observing FAD fluorescence in reference tissue including the test tissue sample itself and reference tissue having a tumor component.

Moreover, changes in fluorescent intensity and lifetime components are increased in invading cells when compared to cells in the primary tumor mass. The changes in endogenous fluorescent properties can be used to help identify, characterize, and stage mammary tumors in animal models and human breast tumors.

The invention is further described by the following non-limiting Examples.

EXAMPLE 1

Collagen Density Promotes Mammary Tumor Initiation and Progression

Abstract

Mammographically dense breast tissue is one of the greatest risk factors for developing breast carcinoma. Despite the strong clinical correlation, breast density has not been causally linked to tumorigenesis, largely because no animal system has existed for studying breast tissue density. Thus, the influence of the extracellular-matrix on breast carcinoma development and the underlying molecular mechanisms are not understood. Importantly, areas of high breast density are associated with increased stromal collagen. In this Example we demonstrate that increased stromal collagen in mouse mammary tissue increases tumor formation ~3-fold and results in a more invasive phenotype. Using nonlinear optical imaging approaches we demonstrate that local invasion is facilitated by stromal collagen re-organization and that this behavior is increased in collagen dense tissues. Additionally, we identify a metabolic signature in invading metastatic tumor cells and show that increased lung metastases result from tumors that progressed in a collagen-dense microenvironment. Hence, this Example provides the first data causally linking increased stromal collagen to tumor formation and metastasis.

Introduction

Mammographically dense breast tissue is linked to a greater than four-fold increased risk of breast carcinoma[1-3], and is one of the greatest independent risk factors for breast cancer[1,2]. For instance, breast density in more than 50% of the tissue may account for up to 30% of breast cancers, while BRCA1 and BRCA2 mutations, though conferring a greater relative risk, account for only 5% of breast cancers (see Boyd et al[4] and references therein). Furthermore, high breast tissue density is associated with a shift to more malignant tumors[5], and ductal carcinoma in situ (DCIS), a local precursor to some invasive breast cancers, arises overwhelmingly in dense regions of the breast.[6] Breast tissue density, which is additionally increased with hormone replacement therapy[7], is further linked to an increased likelihood of DCIS[5,8], invasive breast carcinoma[8,9], lymphatic and vascular invasion[10], and ~three-fold greater risk of developing a second breast carcinoma[9]. However, although there is considerable correlative data identifying breast density as a risk factor for developing carcinoma, the molecular mechanisms driving breast density-related tumor formation and progression remain largely unknown.

Importantly, areas of increased breast density are not only associated with increased epithelial and stromal cellularity[11-13], but also significantly increased fibrillar collagen deposition[5,12,13]. In addition it has been reported that levels of total collagen increase as radiographic breast tissue density increases[5,12]. This is significant since tissue microenvironments play an important role in maintaining normal cellular behavior[14,15], and stroma surrounding breast epithelial cells is believed to be critically involved in epithelial transformation, carcinoma growth, and metastasis[16-19]. Consistent with this concept, adipose-derived type VI collagen promotes tumor growth[20], while disturbing the epithelial-stromal interaction by disrupting the β1-integrin in mammary epithelial cells inhibits tumorigenesis[21]. A less considered aspect of the complexity of the epithelial-stromal interaction is the fact that the stroma is a dynamic mechanical microenvironment, with dense collagenous stroma transmitting multi-axial deformations to breast cells during tissue deformation and increasing resistance to cellular contractility. Such mechanical signals arising from increased density or rigidity of the microenvironment play a role in the transformed phenotype of breast epithelial cells[22,23]. Hence, although tumor formation is a multistep process involving genetic alterations of the epithelial cell, it has become clear that the epithelial-stromal interaction plays a crucial role in tumor formation and progression. Therefore, due to the increased stroma associated with breast tissue density we hypothesized that increasing collagen density in the mammary gland would promote tumorigenesis. Although there is a strong correlative link between breast density and carcinoma, to date collagen density has not been causally linked to tumorigenesis, largely because studies utilizing animal models with different stromal density have not been previously performed. Here we demonstrate that mammary tumor formation, invasion, and metastasis are enhanced in collagen-dense stroma in a transgenic mouse model.

Results

Increased Tumor Incidence in Collagen Dense Mammary Tissues

Figure 2A:
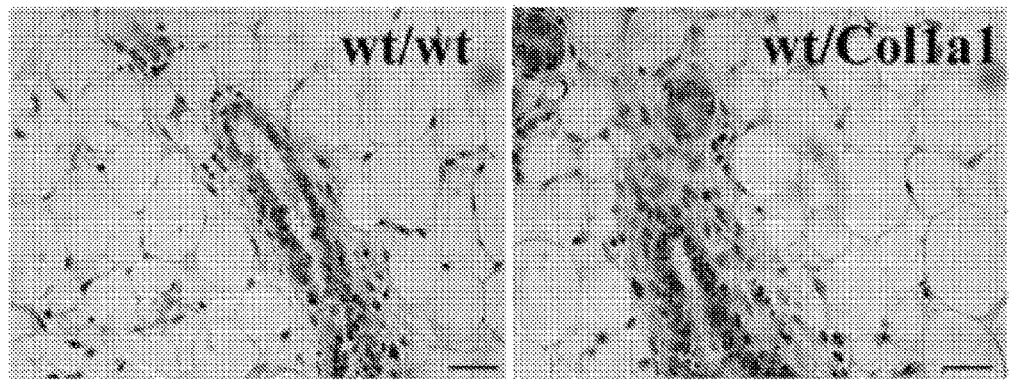
FIG. 2. High mammary collagen density promotes tumor formation. (a) Histology of mammary glands from 10-week-old wild-type and heterozygous Col1a1$^{tmJae}$ mice showing increased stromal collagen and hypercellularity associated with the Col1a1$^{tmJae}$ mouse model. Scale bar=25 µm. (b) Significantly increased tumor incidence in collagen dense (Col1a1) mammary glands. (c) Whole mount preparations of the 4th inguinal mammary glands from PyVT/wt and PyVT/Col1a1 mice at 10 weeks of age. Quantitative analysis of the area of hyperplasia from three pairs of glands calculated from a common threshold value set with density slicing in ImageJ software revealed a greater than 1.5-fold increase in hyperplasia associated with increased stromal collagen (t-test: p=0.03). Additionally, at age-matched time points, tumors in mice with dense stroma not only displayed more hyperplastic area but also tumor regions that grew out away from the gland (arrow in c; and d). (e) Low (i-ii) and high (iii-iv) magnification images of H&E stained histology sections from 10 week old mice showing increased collagen in PyVT/Col1a1 tumors (ii and iv) and a more invasive phenotype when compared to PyVT/wt (i and iii) tumors. Scale bars=50 µm (i-ii) and 25 µm (iii-iv).

In order to develop a murine tumor model possessing collagen-dense mammary tissue, we examined the mammary tissues from Col1a1$^{tmJae}$ transgenic mice (FIG. 2a). These mice carry mutations near the highly conserved matrix metalloproteinase (MMP) cleavage site for type I collagen (between $Gly_{775}$ and $Ile_{776}$ of the α1(I) chain) that make the collagen resistant to human collagenase digestion[24]. Although an additional cleavage site on type I collagen is vulnerable to rodent collagenase (often termed rat collagenase) and the collagen is susceptible to other proteases[24], these are not sufficient to achieve the proper balance of collagen synthesis and degradation, resulting in excessive collagen accumulation in the skin, uterus, and bone[24]. These phenotypes raised the possibility that the mammary gland, which undergoes dynamic changes in collagen deposition and degradation during development, puberty, and estrous, would rapidly accumulate excess stromal collagen. To explore this possibility, we previously analyzed mammary glands from wild-type, heterozygous, and homozygous Col1a1$^{tmJae}$ mice and reported a greater than 2.5 fold increase in stromal collagen associated with heterozygous and homozygous mice[25] (FIG. 2a).

Figure 2B:
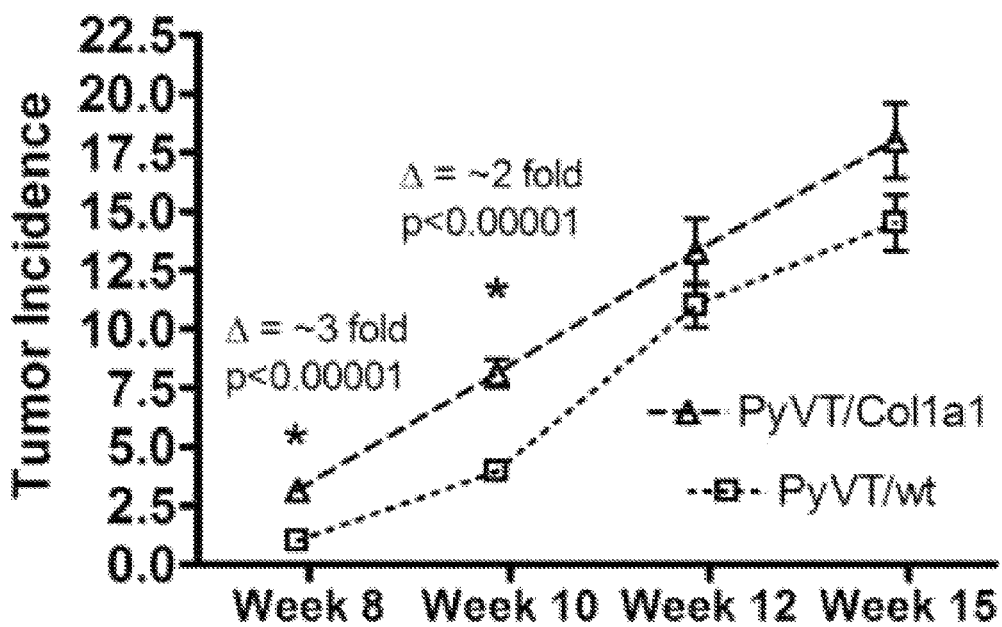
Figure 2C:
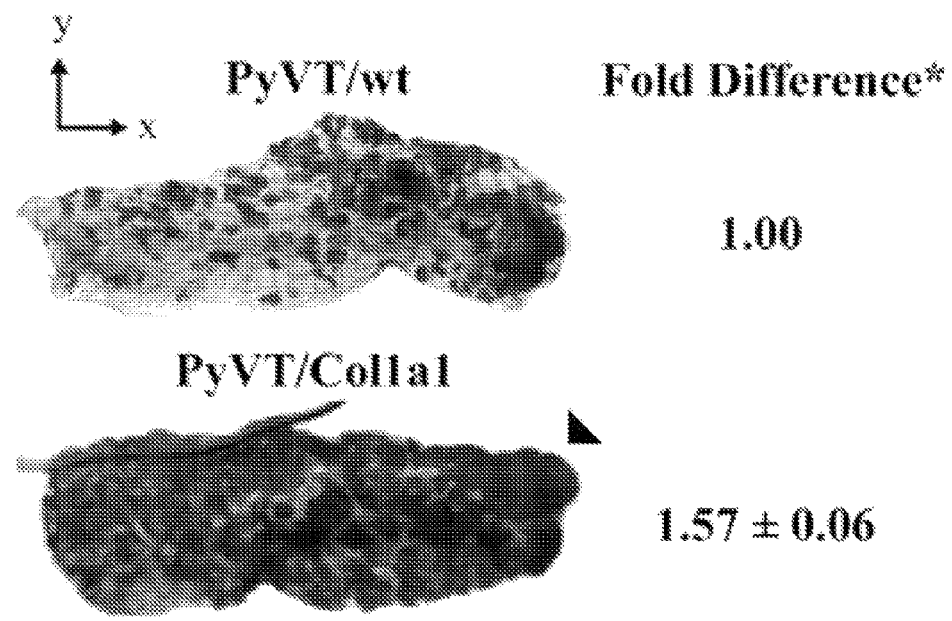
Figure 2D:
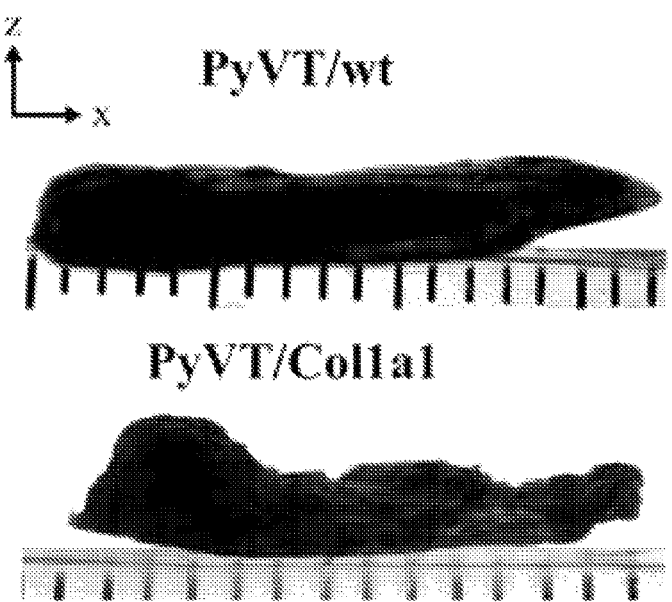
Figure 2E:
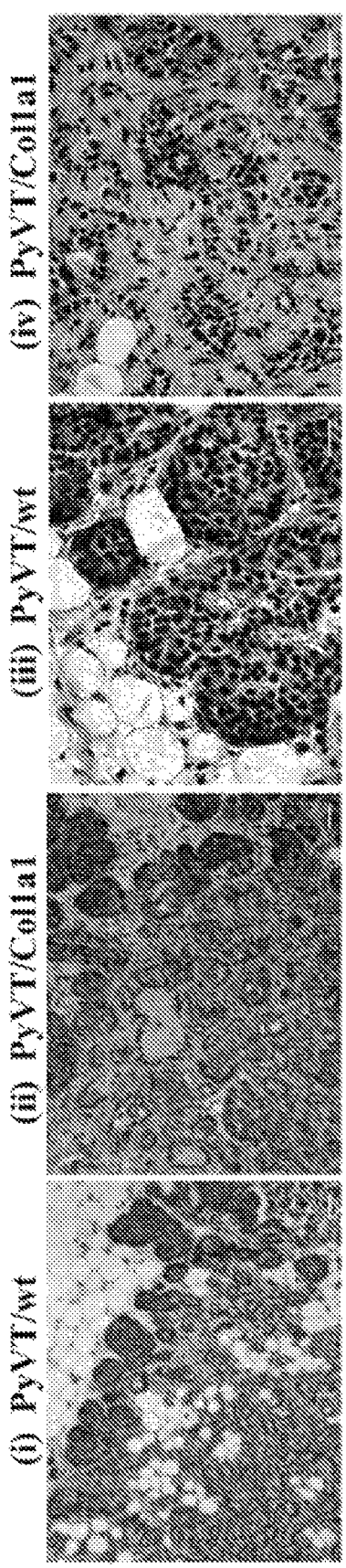

With a defined model for breast tissue density in place, we set out to test the hypothesis that increased mammary collagen density increases tumor formation. Mammary tumors were initiated with the polyomavirus middle-T (PyVT) transgene. This breast tumor model correlates well with many features of human cancer, progresses from hyperplasia to adenoma to early and late carcinoma[26], and is reliably invasive and metastatic[26]. When mice carrying the PyVT transgene under the control of the mammary epithelial-specific MMTV promoter were crossed with heterozygous Col1a1$^{tmJae}$ mice, we observed an approximately three-fold increase in early tumor formation in collagen-dense tissues (FIG. 2b). This trend of increased tumor incidence in collagen-dense glands continued through week 15 (FIG. 2b), with two additional PyVT/Col1a1 mice requiring euthanasia by week 13 due to excessive tumor burden (not shown). Consistent with these observations, quantitative analysis of whole mounts of the 4th mammary gland (n=3 pairs) show significantly increased areas of hyperplasia (FIG. 2c) with collagen-dense tissues showing increased growth out from the gland (FIG. 2c arrowhead and FIG. 2d). Furthermore, tumors progressing in collagen-dense tissues at 10 weeks had a more invasive morphology (FIG. 2e). Of note is the fact that tumors arising in collagen dense mammary tissue retain increased collagen density (FIG. 2e and confirmed with collagen selective picrosirius red staining: not shown). In fact, collagen levels in PyVT/Col1a1 tumor-bearing glands appear to be increased relative to non-tumor bearing collagen dense glands (FIG. 2e). This observation possibly indicates an amplified shift in the unbalance between collagen synthesis and degradation in the Col1a1 mice following tumor initiation, and may represent an increased desmoplastic response.

Figure 3A:
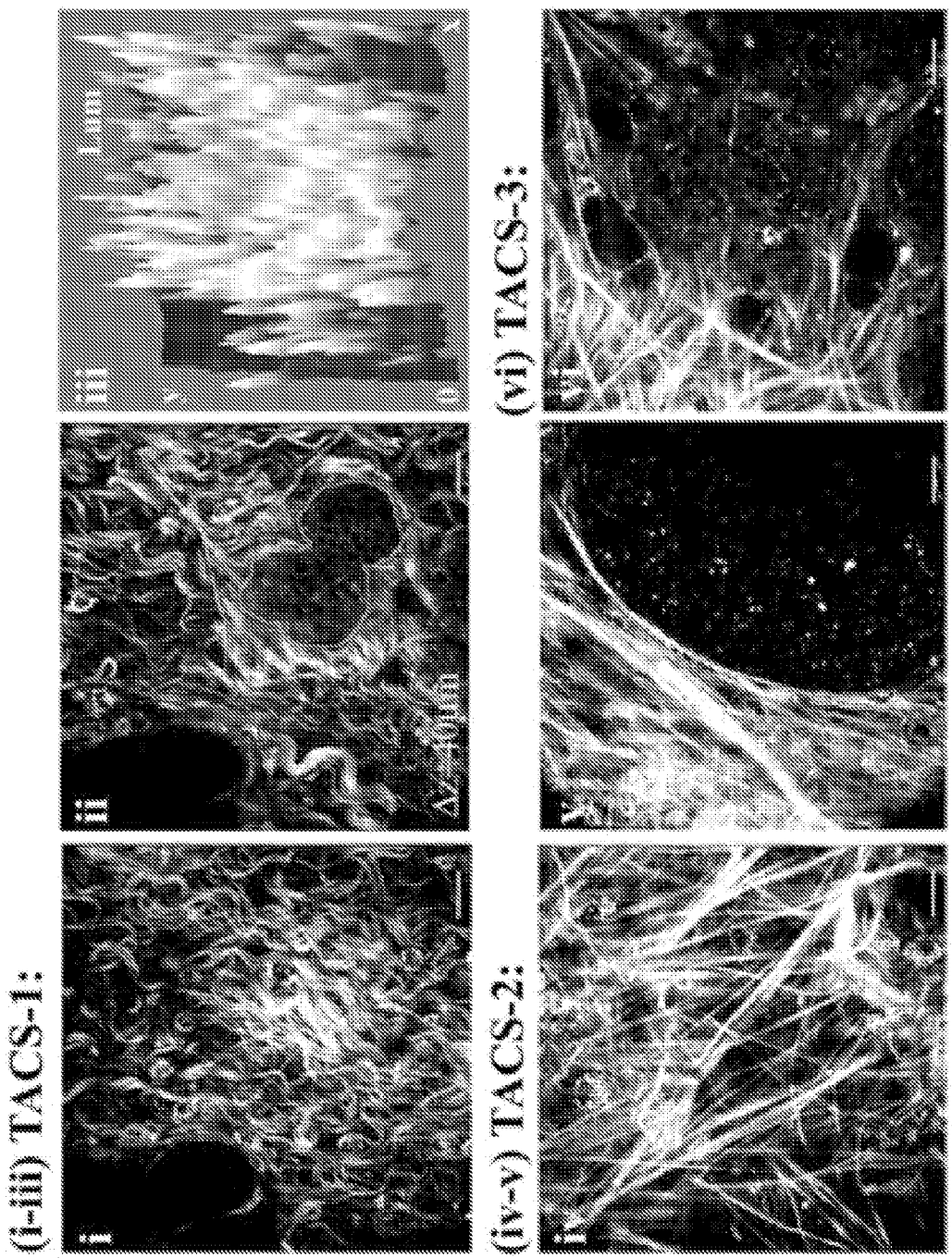
FIG. 3. Tumor Associated Collagen Signatures (TACS) and Increased Local Invasion with High Collagen Density. (a) Example of TACS-1 (i-iii). A region of locally dense collagen (i) near a small tumor region (ii) that is within the globally increased collagen region surrounding tumors, resulting from increased SHG (collagen) signal intensity (iii; 3D surface plot of luminescence (Lum) showing an ~3-fold signal increase at TACS-1). Example of TACS-2 (iv-v), showing straightened (taut) collagen fibers stretched around and constraining an expanded epithelial tumor volume. At regions of TACS-2, quantitative analysis[25] of fiber angles relative to the tumor boundary shows a distribution of fibers around 0° that correlates to non-invading regions of tumor cells. Example of TACS-3 (vi), showing radially aligned collagen fibers, reorganized by tumor cells, at regions of tumor cell invasion. At regions of TACS-3, quantitative analysis[25] of fiber angles relative to the tumor boundary shows a distribution of fibers around 90° that correlates with local invasion of tumor cells. (b) TACS-1 in 8 week old normal (wt; i-ii) and collagen dense (Col1a1; iii-iv) tumors showing more developed TACS-1 associated with density (early transition between TACS-1 and -2) while showing very early TACS-1 formation in wild-type tumors (yellow arrowheads; white arrowhead indicates a TACS-1 region that is not shown since it is out of the focal plane). The displayed tumor regions (i and iii) are at a Δz=40 µm from collagen signatures (ii and iv). Note the increased endogenous cellular autofluorescence associated with tumor cells in collagen-dense tissues when PyVT/wt (ii) and PyVT/Col1a1 (iv) tumors were imaged sequentially at the same power settings (ii versus iv). Representative of n=4 pairs of tumors. (c) Tumors were imaged and MPE (red) and SHG (green) signals were separated. Top panels: 8 week old tumors showing early TACS-3 regions and some local invasion in collagen dense tumors (PyVT/Col1a1) while PyVT/wt tumors were still primarily bound by collagen (TACS-2) and non-invasive. Bottom panels: 10 week old tumors from dense tissues (PyVT/Col1a1) displayed further regions of TACS-3 progression and an invasive phenotype, compared to control tissues (PyVT/wt) that were largely non-invasive and had little collagen reorganization. Representative of n≧6 tumors from each background. (d) Quantitative analysis of collagen fiber angles relative to the tumor boundary for 8 week (top) and 10 week (bottom) old animals. PyVT/wt animals displayed little TACS-3 and are primarily non-invasive with only 23% (8 weeks) and 24% (10 weeks) of their fibrils having angles outside of the TACS-2 distribution around 0° (i.e. <−15° or >15°). In contrast PyVT/Col1a1 tumors had some regions of TACS-3 (distribution around 90°) and local invasion with 46% of the fibril distributed outside of the TACS-2 distribution (0°) at 8 weeks. At 10 weeks, PyVT/Col1a1 tumors were more invasive and had a broader distribution of TACS-3 with 51% of fiber angles outside of the TACS-2 distribution. Calculated from ≧185 of tumor regions from ≧6 separate tumors. All scale bars=25 µm.
Figure 3B:
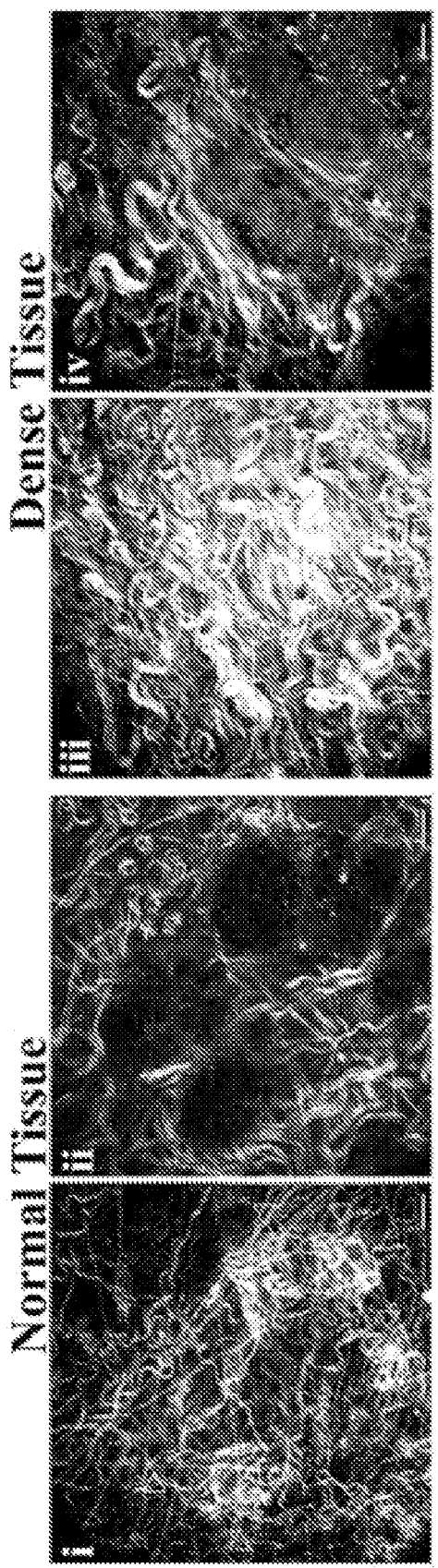
Figure 3C:
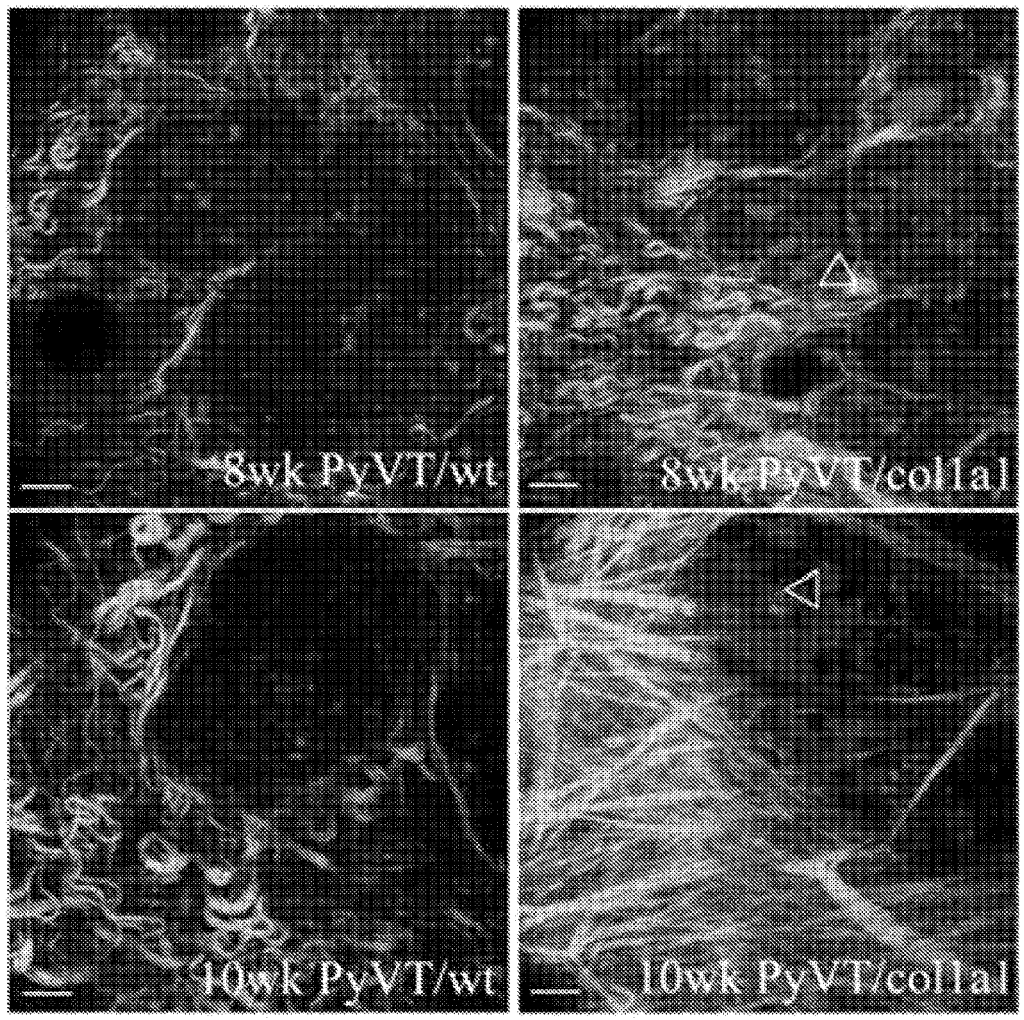
Figure 3D:
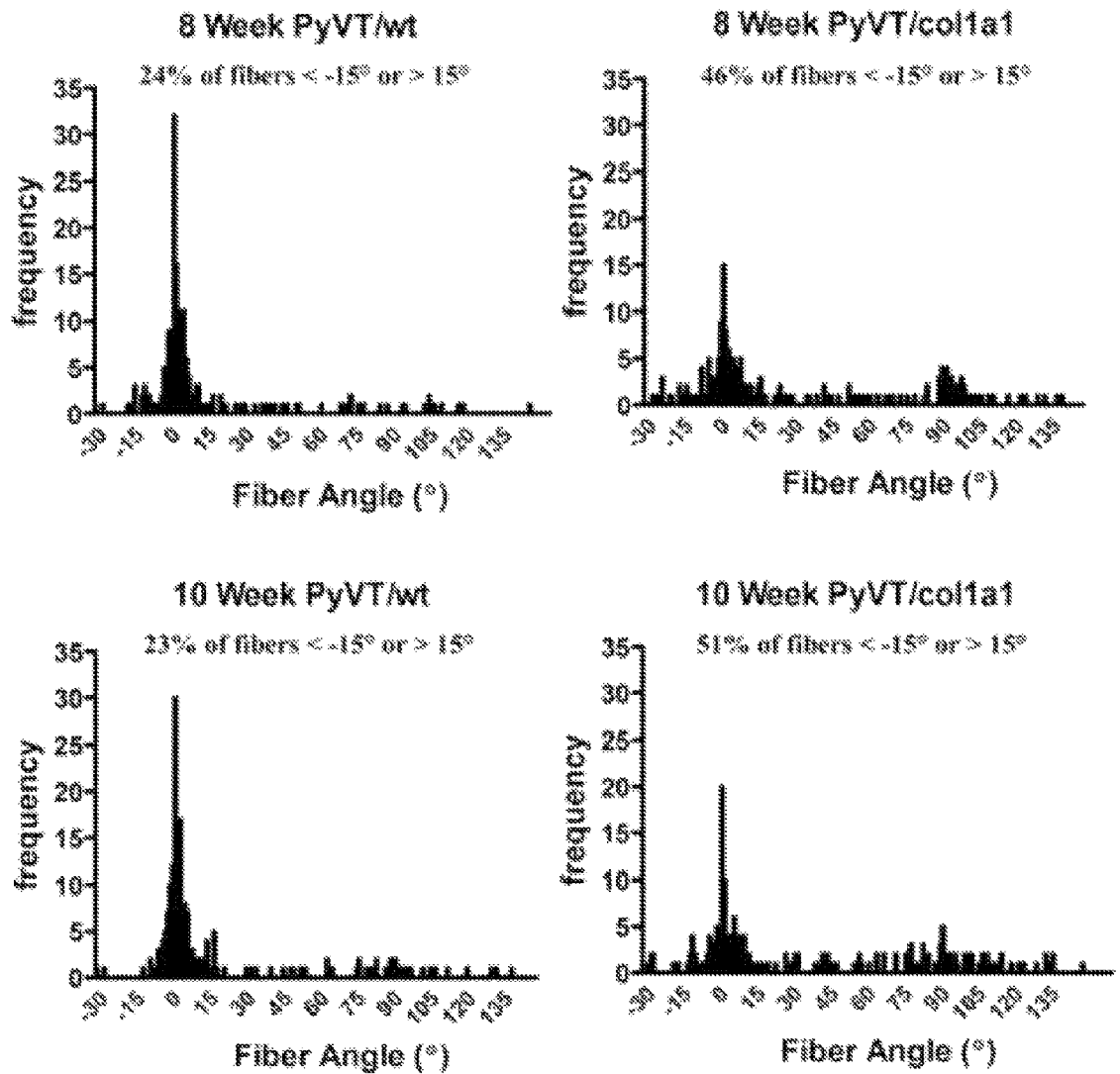

Changes in the Tumor-Stromal Interaction Associated with Increased Stromal Collagen Collagen content, fiber structure, and organization are potentially key determinants of tumor cell behavior[25,27]. Therefore, to better understand the tumor-stromal interactions associated with collagen density we employed nonlinear optical imaging of intact live tumors. Multiphoton laser-scanning microscopy (MPLSM) was used to simultaneously generate intrinsic signals from cellular autofluorescence by multiphoton excitation (MPE) and fibrillar collagen by second harmonic generation (SHG)[25,28-30]. Using this approach we previously defined[25] three Tumor-Associated Collagen Signatures (TACS; FIG. 3a) in mammary tumors from both Wnt-1 and PyVT transgenic mice. Specifically, TACS-1: the presence of locally dense collagen (FIG. 3a-i) within the globally increased collagen concentration surrounding tumors, indicated by increased signal intensity (FIG. 3a-iii) at a region near the tumor, which serves as a reliable hallmark for locating small tumor regions (FIG. 3a-ii); TACS-2: straightened (taut) collagen fibers stretched around the tumor, constraining the tumor volume (FIG. 3a-iv and -v); and TACS-3: identification of radially aligned collagen fibers that facilitate local invasion (FIG. 3a-vi). With TACS-3, a distribution of collagen fiber angles around 90° relative to the tumor boundary was indicative of high levels of local invasion while a distribution around 0° was associated with non-invading regions of the tumor[25]. In comparing tumors in the wild-type and heterozygous Col1a1$^{tmJae}$ backgrounds carrying the MMTV-PyVT transgene, we identified critical differences in the temporal progression in density-associated tumors (FIG. 3b-d). At 8 weeks of age, TACS-1 formation in wild-type tumors (FIG. 3bi-ii;) was not yet well developed, and tumors were primarily non-invasive with collagen fibers distributed around 0° (FIG. 3c-d). In contrast, collagen-dense tumors (PyVT/Col1a1) displayed more developed TACS-1 with increased collagen signal and more straightened fibers, indicating early progression to TACS-2 (FIG. 3biii-iv) and some regions of TACS-3 (FIG. 3c). Dense tissues (PyVT/Col1a1) began to show regions of local invasion at 8 weeks (FIG. 3c; highlighted with arrowhead) corresponding to an increased frequency of reorganized collagen fibers with a peak realignment near 90° (FIG. 3d). By 10 weeks of age this difference was enhanced. While tumors from PyVT/wt animals were still largely non-invasive, tumors that arose in collagen-dense tissues continued to have more collagen signal, enhanced realignment to TACS-3, and increased local invasion (FIGS. 3c and d), supporting histological findings shown in FIG. 2e. Moreover, this shift in the temporal onset of TACS-3 to an earlier occurrence in collagen-dense tumors indicates the more advanced and invasive state of these tumors.

In concert with changes in the alignment of stromal collagen and increased local invasion, higher cellular autofluorescence intensity was observed in stromal cells and invading tumor cells when compared to cells in the primary tumor mass (FIGS. 3 and 4). To examine these progression-associated changes in more detail, we imaged the tumors with multiphoton fluorescence lifetime imaging microscopy (FLIM) and spectral lifetime imaging microscopy (SLIM). Using these techniques, we were able to further confirm the presence of collagen, which has a theoretical zero lifetime that experimentally equals the system signal response due to background noise (100 ns (dark) in FIG. 4a). The spectral properties of the endogenous cellular fluorophore identify it as FAD (FIG. 4b and FIG. 6).

Figure 4A:
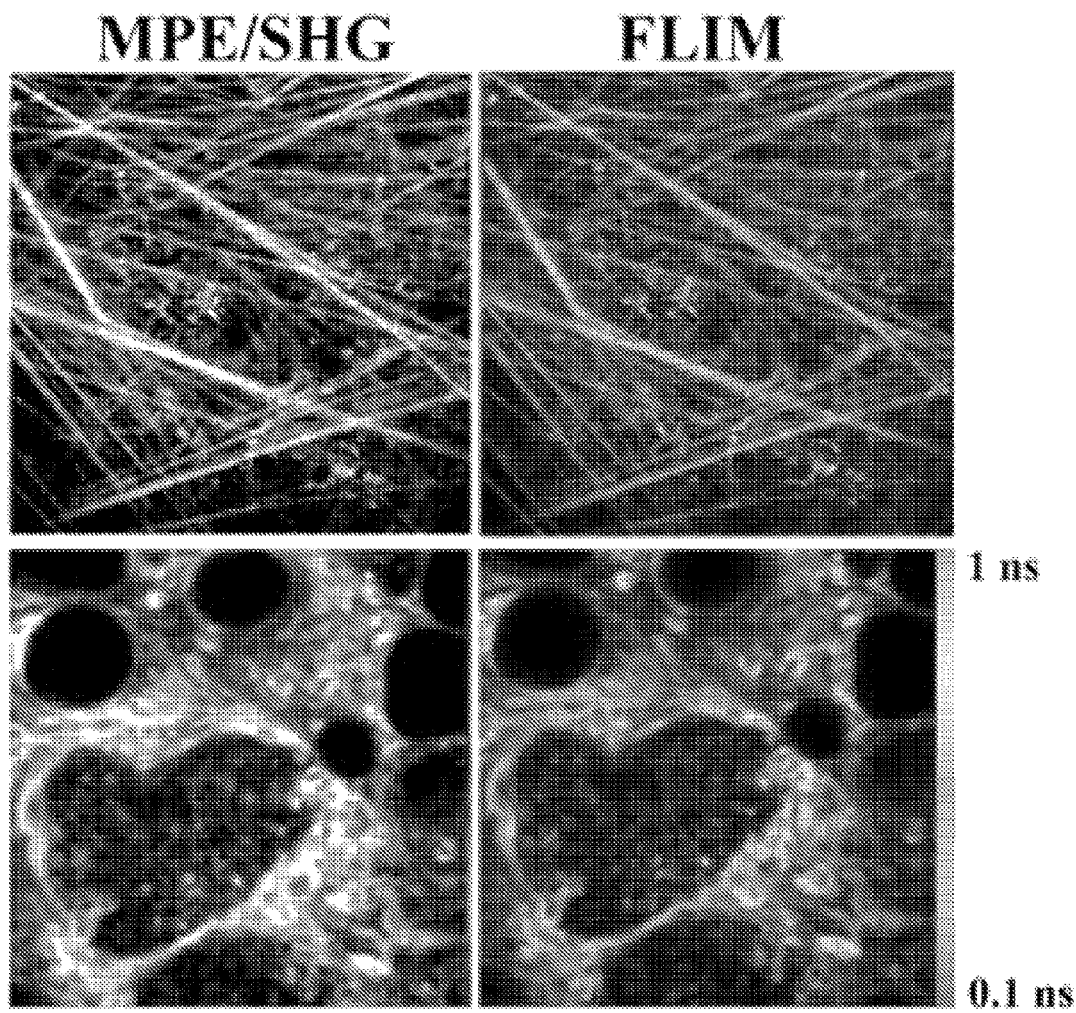
FIG. 4. FLIM and SLIM Analysis of Invading Tumor Cells. (a) Multiphoton intensity and fluorescence lifetime imaging microscopy (FLIM) images of the stroma near a tumor (top) and the tumor and stromal components (bottom) from wild-type tumors showing the utility of FLIM to image tumor cells, stromal cells, and extracellular matrix components. Note the increased intensity and fluorescent lifetimes of stromal cells (quantified in c) and the low lifetime of collagen (matching system response, i.e. no actual lifetime). The grayscale map in (a) represents the weighted average of the two-term model components $[\tau_m=(a_1\tau_1+a_2\tau_2)/(a_1+a_2)]$ using the equation shown in (c). (b) Multiphoton spectral lifetime imaging microscopy (SLIM) analysis of the emission spectrum from endogenous fluorescence resulting from excitation at 890 nm. The emission signals were separated by 10 nm spectral steps over 16 channels (10 channels are displayed) and the photons collected in each channel used to generate fluorescence lifetime images and signals for each channel plotted with SLIM-Plotter (shown). Emission from collagen (at half of the input wavelength) showed a very strong and sharp signal with a no appreciable decay (lifetime) confirming the SHG nature of the collagen signal (top). Emission spectra of endogenous fluorescence from tumor and stromal cells showed that the only substantial emission signal is at 530 nm, indicating that the source of the autofluorescence signal is FAD, and not NADH or tryptophan[50], with lifetime values from the 530 channel matching values obtained with FLIM. (c) Quantitative analysis of fluorescent lifetime components from tumor and stromal (subscript s) cells using the equation shown. Note the increase in the second (long) component and weighted mean values component (see equation above) for stromal cells when compared to cells from the primary tumor mass. Note, ≧30 measurements per tumor image from 4 independent tumors were used to calculate lifetime values for tumor cells in the primary tumor mass while ≧6 measurements per tumor image from 4 independent tumors were used for stromal cells. (d) Intensity and FLIM images of cells away from and near invasive TACS-3 regions showing increased fluorescent intensity and lifetime near invasive regions (left side of images). (e) FLIM images of tumors from 10 week old PyVT/ wt and PyVT/Col1a1 animals confirming the increased TACS-3 for collagen dense tumors shown in FIG. 2. Note the increased fluorescent lifetimes for invading cells (right panel) quantified in f. Like stromal cells the second (long) and mean component are increased in invading cells. However, the short component is also increased in invading cells when compared to cells in the primary tumor mass. Note, 45 measurements for cells within the primary tumor mass and 45 measurements for invading cells adjacent to the tumor primary tumor mass were used to calculate lifetime values. (g) The second (long) component from cells with the primary tumor mass, invading tumor cells, and stromal cells showing a progressive increase as cells move from a primary epithelial tumor phenotype to a more mesenchymal phenotype. (h) 3D tumor cell invasion assay showing that tumor explants from collagen dense tumors (PyVT/Col1a1) resulted in more invasion into 3D collagen gels and colony formation after 10 days than explants from PyVT/wt tumors (mean ±SEM; n=4 PyVT/wt and n=14 PyVT/Col1a1 tumor explants from four sibling mice). *Indicates a statistically significant ($p<0.05$) difference following analysis with 1-way Analysis of Variance (ANOVA) with a post-hoc Tukey-Kramer test for c, f, and g, and a paired t-test for h.
Figure 4B:
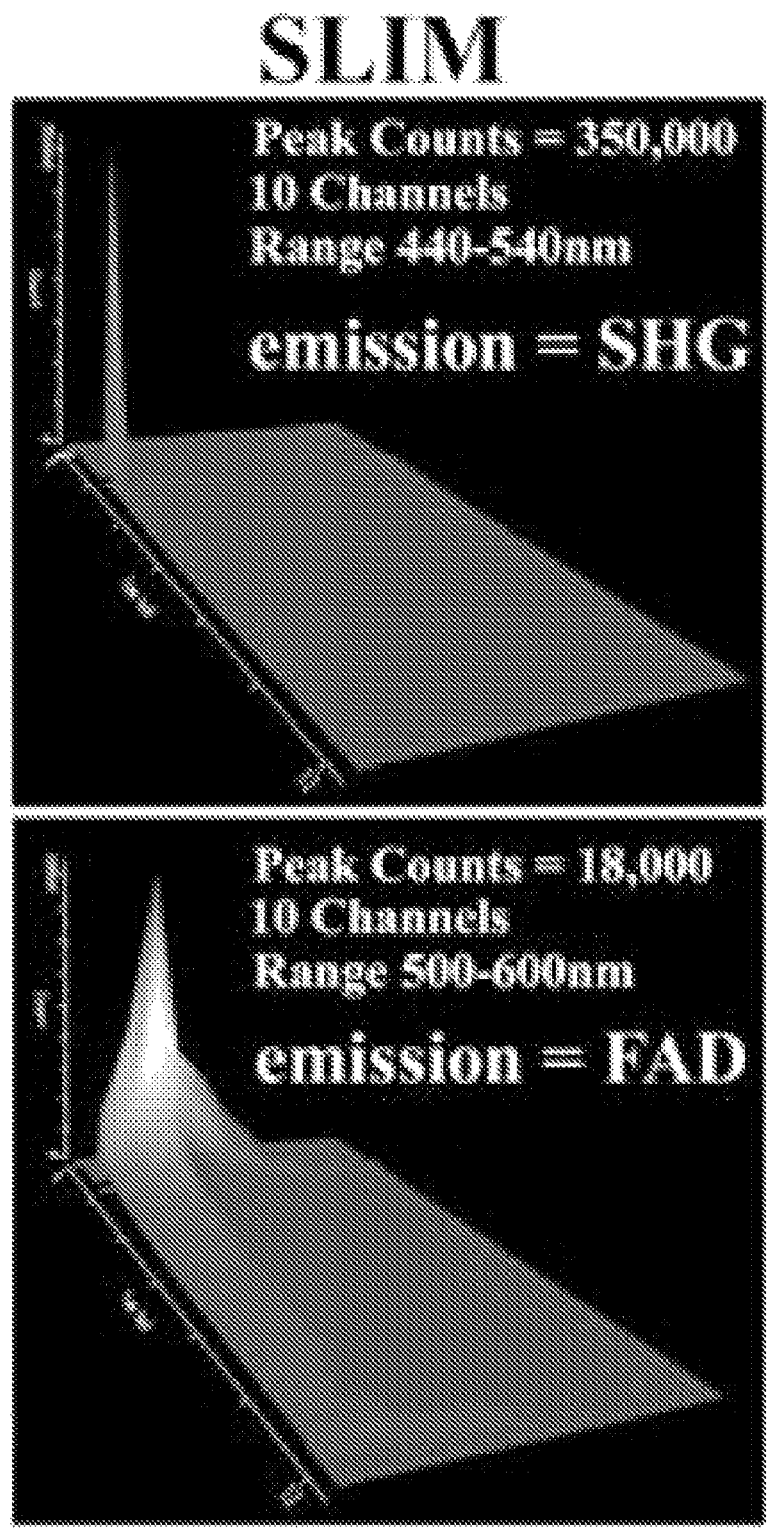
Figure 4C:
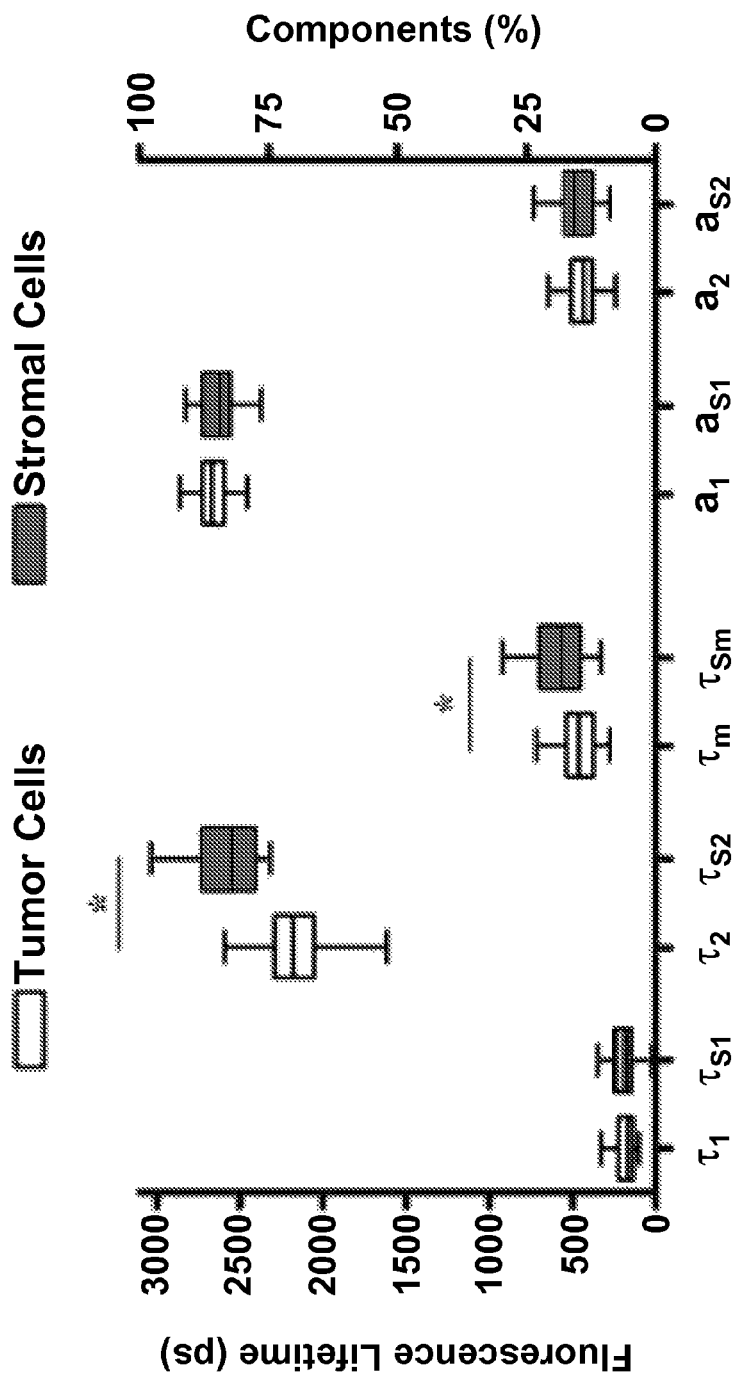
Figure 4D:
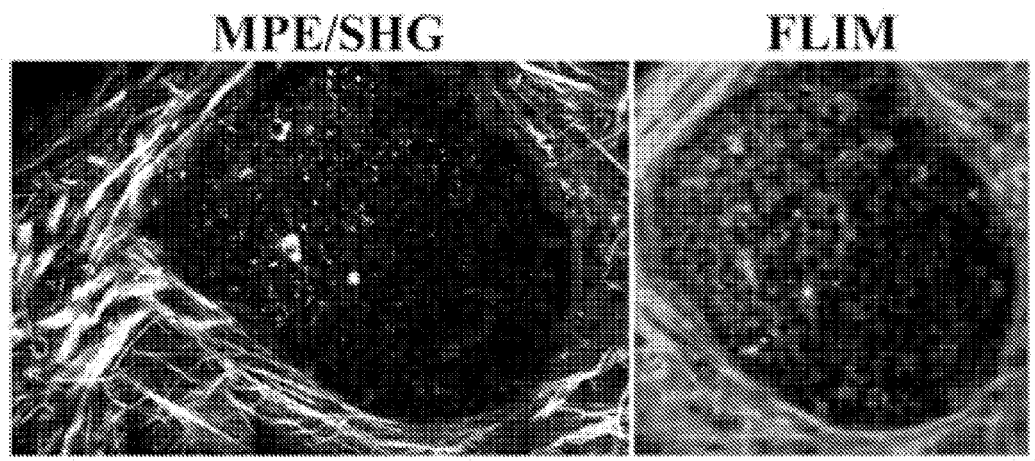

Exploiting cellular FAD as an endogenous biomarker to visualize cells, we further explored the difference in FAD signal between stromal and tumor cells, using FLIM. Differences in the fluorescence lifetime of FAD between primary tumor cells and stromal cells were greyscale mapped (FIG. 4a) and quantified (FIG. 4c). Stromal cells possessed a higher second component ($\tau_2$) and weighted mean values ($\tau_m$) of the fluorescent lifetime, allowing stromal cells to be easily differentiated from epithelial tumor cells (FIGS. 4a and c). Interestingly, invading cells displayed a fluorescent intensity more closely resembling stromal cells than cells from the primary tumor mass (FIGS. 4d and e). Consistent with this finding, changes in fluorescent intensity and fluorescent lifetimes of NADH and tryptophan have also been associated with cells of differing metastatic potential[31]. Because invading tumor cells commonly undergo an epithelial-to-mesenchymal transition (EMT), it is possible that shifts in the fluorescent lifetime may be indicative of EMT. In fact, higher FAD fluorescent intensity was observed in cells near invading regions when compared to non-invading regions (FIG. 4d) while invading tumor cells showed a longer FAD fluorescent lifetime (FIG. 4e—right panel), having higher first ($\tau_1$), second ($\tau_2$), and weighted mean values ($\tau_m$) lifetime components (FIG. 4f), and could be differentiated from stromal cells and cells in the primary tumor mass. Additionally, examination of $\tau_2$ values indicates a progressive increase in lifetimes from cells within the tumor mass to invading cells to stromal cells (FIG. 4g) supporting the idea that an EMT may be taking place.

Increased Invasion and Metastasis Associated with Dense Stromal Collagen

Figure 4E:
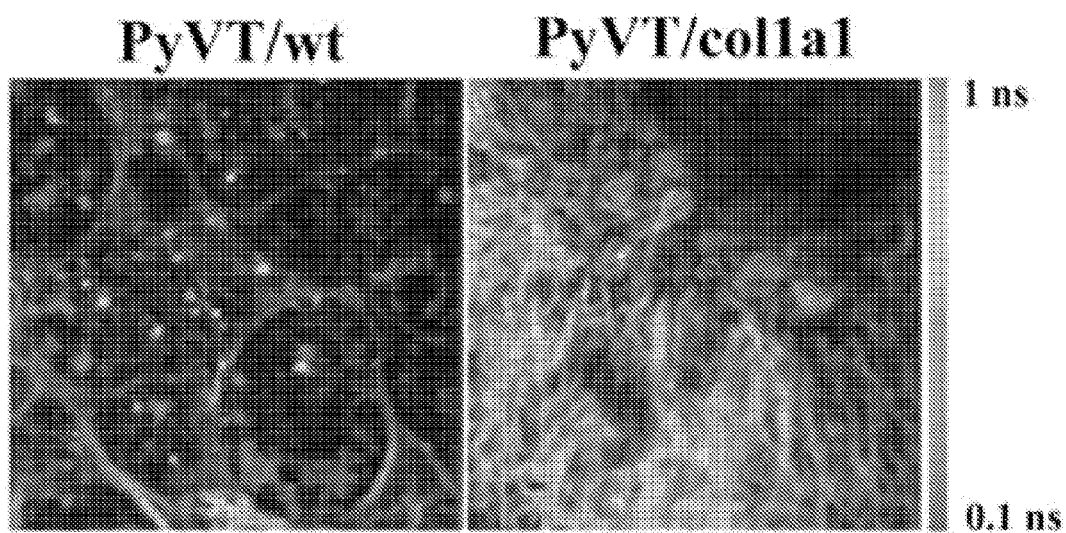
Figure 4F:
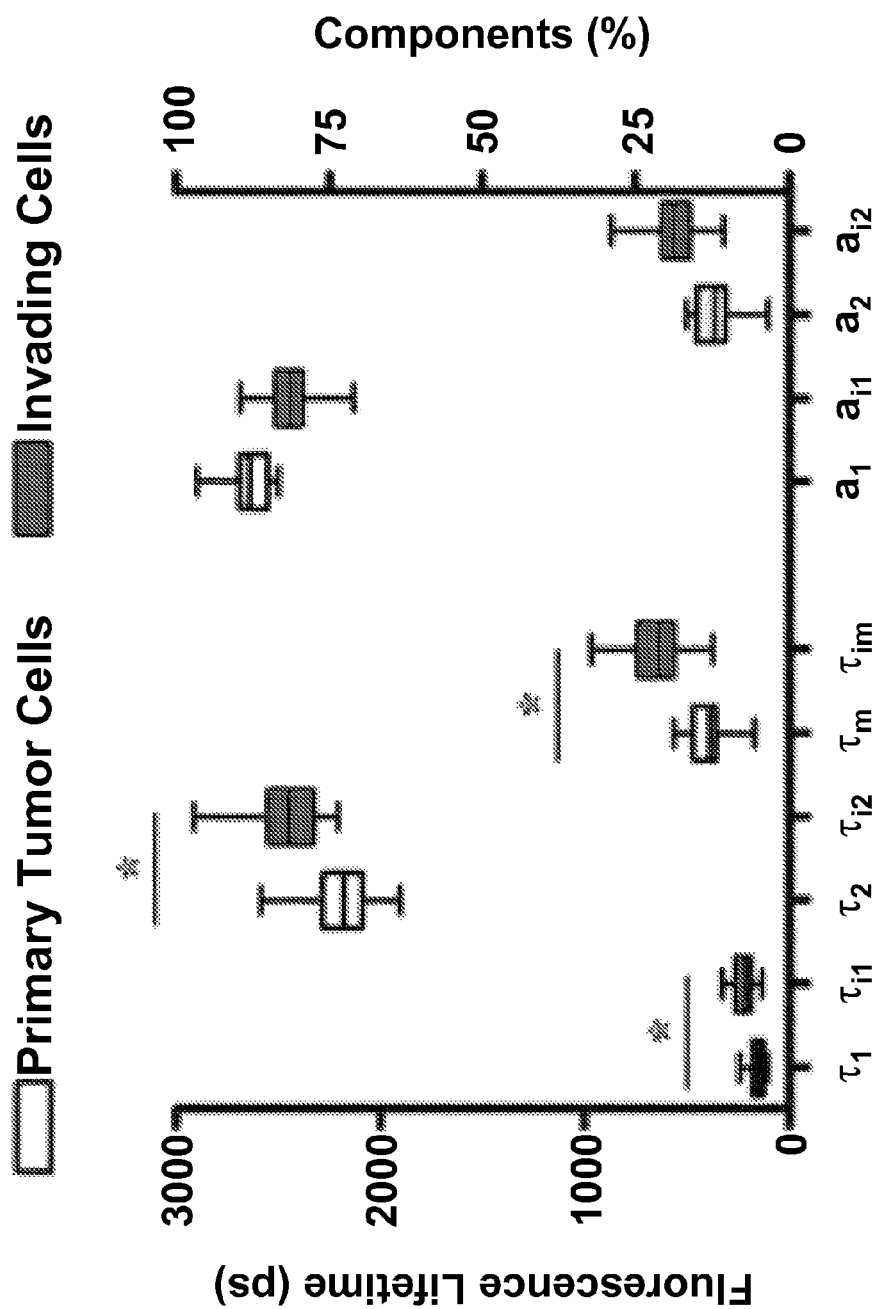
Figure 4G:
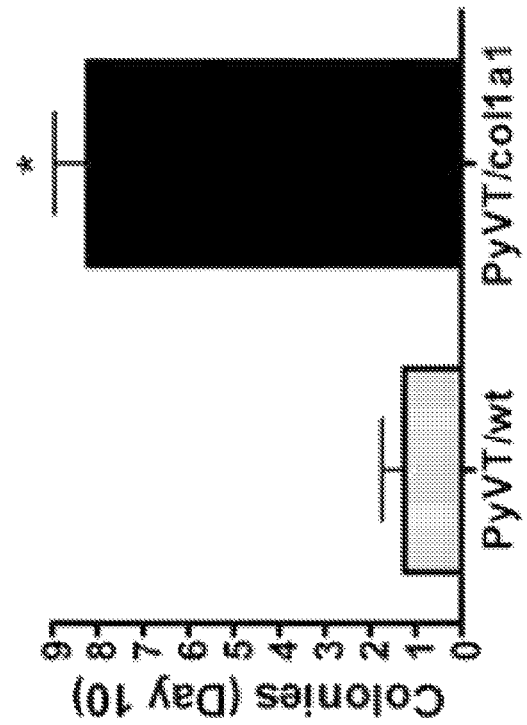
Figure 4H:
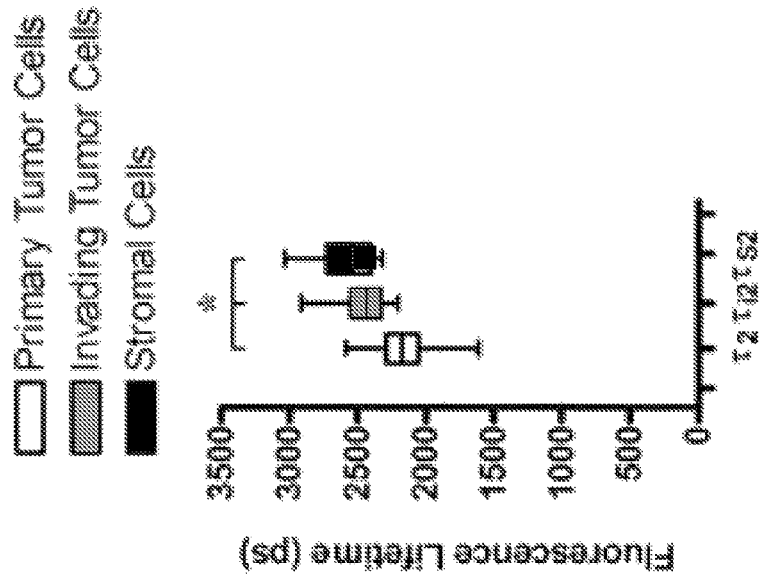

In addition to identifying key differences in measurable fluorescent intensity and lifetime associated with invading cells, FLIM analysis confirmed results shown in FIG. 3 demonstrating a shift towards TACS-3 and increased local invasion with higher collagen density (see FIG. 4e). Invading cells associated with TACS-3 could be clearly differentiated in collagen-dense tissues (FIG. 4e-right panel) while PyVT/wt tumors (FIG. 4e-left panel) were non-invasive at this stage (week 10). Confirmation of increased invasion in tumors that arose in collagen-dense tissue was obtained by examining invasion from tumor explants into 3D collagen gels. Tumor explants of defined size were placed into 3D collagen gels and the number of distant colonies was counted. After 10 days in culture, explants from collagen-dense tissues resulted in significantly more colonies (FIG. 4h) corroborating data from live tissues (FIGS. 3 and 4) that tumors associated with collagen dense tissues are more invasive.

Figure 5B:
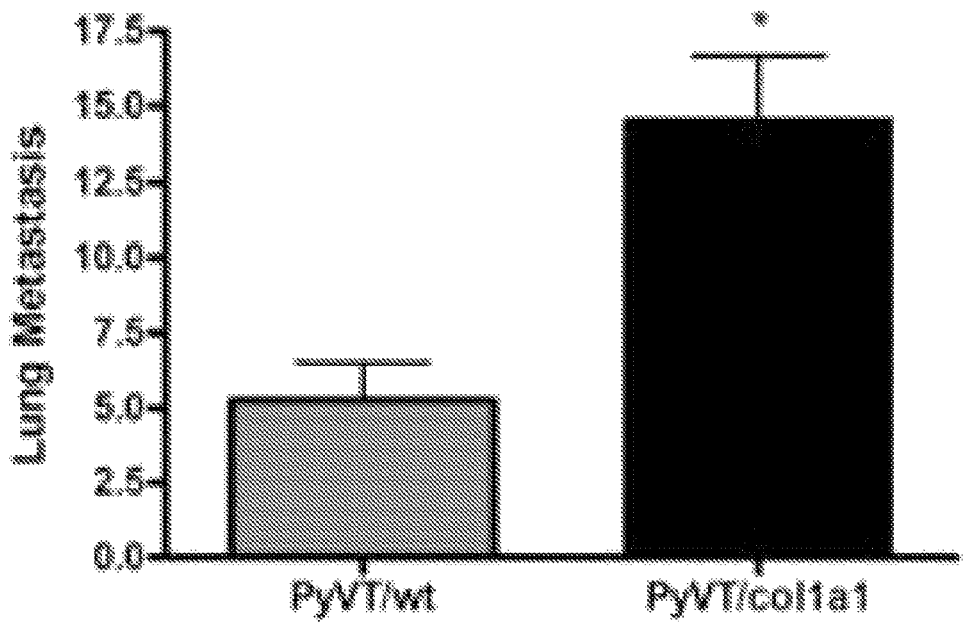
Figure 5C:
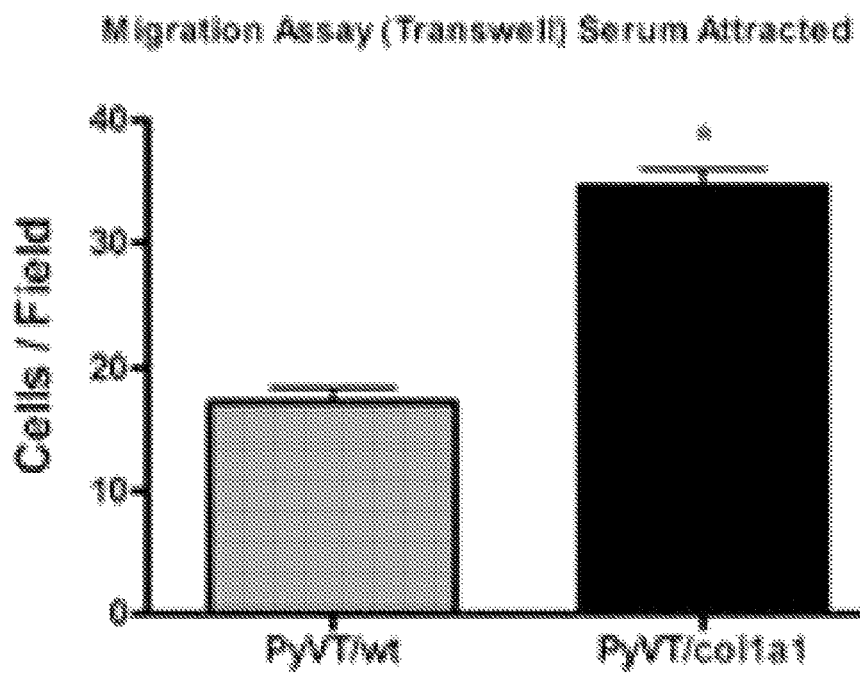

Examination of later stage tumors (week 15) demonstrated that both PyVT/wt and PyVT/Col1a1 tumors were invasive and possessed regions of TACS-3 mediated invasion (FIG. 5a), confirming an earlier report that late stage wild-type PyVT tumors have invasiveness associated with TACS-3[25]. Moreover, since the MMTV-PyVT tumor model reliably results in lung metastases we examined lung tissue in late stage mice (week 15). In animals in which tumors were initiated and progressed in a collagen-dense microenvironment, significantly increased lung metastases were observed (FIG. 5b). This raised the possibility that increased lung metastasis may be the result of a more invasive and migratory cell population, or may result from the earlier onset of invasiveness as seen in FIGS. 2-4. To address this question, we isolated tumor cells and performed migration assays over the first 24 hours following tumor harvest. Tumor cells isolated from collagen-dense tissues were in fact more migratory (FIG. 5c), indicating that the earlier onset of invasiveness is likely not the sole cause for increased metastasis but that the tumor cells themselves are more invasive (FIG. 4h) and migratory (FIG. 5c).

Discussion

Although the increased risk for breast carcinoma associated with collagen-dense breast tissue has been described[1-3], little is known of the molecular mechanisms underlying increased collagen deposition and its influence on the interactions between stromal collagen, fibroblasts, and epithelial cells, nor how increased collagen affects tumorigenesis. This is due in large part to the fact that no animal model system had previously existed to study these phenomena in vivo. Herein we demonstrate that mice with increased stromal collagen have increased mammary tumors that are more invasive and metastatic, consistent with reports of the human carcinoma progression.

We previously described the use of collagen alignment to quantify local invasion with the level of TACS-2 (alignment tangential to the tumor boundary at a 0° angle) and TACS3 (alignment radial to the tumor boundary at an angle of 90°) providing a novel quantitative assessment of tumor progression[25]. In this study, the analysis of collagen radial alignment in samples from 8 and 10 week tumors demonstrates a transition from TACS-2 to TACS-3. We observe a broad distribution of fiber angles away from zero but not yet tightly grouped at the radial alignment (90°) associated with a high degree of local invasion previously reported for 15 week tumors[25]. This result suggests that the move toward invasive behavior is a transitional process increasing with time. We find that tumor cells in collagen-dense tumors are not only more invasive and metastatic in vivo, but were also more invasive and migratory in vitro (FIG. 4h and FIG. 5c), indicating that the increased invasiveness is not only the result of earlier tumorigenesis that had more time to progress, but also due to tumor cells that are fundamentally more invasive because they arose within collagen-dense tissues. This finding suggests that cellular behavior is altered by epigenetic changes signaled from the collagen-dense stroma, consistent with findings that increased collagen density alters epithelial cell signaling and behavior in vitro[23].

The data of this Example demonstrates that increased stromal collagen in the mammary gland is part of a mechanism that results in increased tumorigenesis and a more invasive phenotype. This may be the result of two likely mechanisms. The first is that increased breast density is associated with a stiffer extracellular matrix resulting in high local mechanical loads and higher resistance to cellular contractility for breast epithelial cells. Such changes in the physical microenvironment has been shown to alter focal adhesion and Rho GTPase signaling, resulting in a more transformed phenotype[22,23]. A second, and more indirect mechanism, may be the influence of increased stromal collagen on mammary fibroblasts that in turn influence epithelial cells. Stromal fibroblasts can regulate epithelial cells in part through secretion of specific soluble growth factors and chemokines[19,32-34]. For instance, TGF-β has been associated with reactive stroma, fibrosis, and epithelial cell invasion[35], while numerous studies indicate that the epidermal growth factor (e.g. EGFR, HER-2/neu/ErbB2, ErbB3 etc.), insulin-like growth factor (e.g. IGF-I, IGFBP3, etc.), and hapatocyte growth/scatter factor (HGF/SF, c-Met) systems are important not only in the normal mammary gland but also during tumorigenesis and metastasis[34,36-39]. Furthermore, the IGF family has been implicated in association with dense breast tissue[13,40,41] with both local[13] and circulating[40,41] levels of IGF-I positively correlated with breast tissue density. In fact, both of these mechanisms are plausible and are likely to be acting in concert with one another to produce fundamental changes in both the breast epithelial and stromal cells. Since both adhesion-mediated and growth factor-mediated signaling pathways are often interrelated[42-47], understanding each of these possible mechanisms and their convergence is likely to be of great importance to understanding breast tissue density-related carcinoma.

In conclusion, increased collagen density increases tumorigenesis, local invasion, and metastasis, causally linking increased stromal collagen to tumor formation and progression. Imaging with combined MPE and SHG in tumors allows visualization of cellular autofluorescence and defined collagen structures that identify key differences associated with high collagen density and may provide useful diagnostic tools to rapidly assess fresh tissue biopsies. Furthermore, imaging live tissues with FLIM and SLIM confirms results obtained with MPE/SHG and identifies significant differences in fluorescence lifetimes that are indicative of invasive cells. Thus, FLIM and SLIM provide effective tools to evaluate the invasiveness of tumor cells in mammary tissues.

Methods

Mice. The University of Wisconsin animal use and care committee approved this study. Breeding pairs of Col1a1$^{tmJae}$ mice[24] in the B6/129 background were obtained from Jackson Laboratory. Male FVB Polyomavirus middle-T mice under the control of the mammary specific MMTV promoter were originally obtained from Dr. Amy Moser (University of Wisconsin) and are abbreviated PyVT following the Jackson Laboratory (from which they originated) nomenclature, but are also commonly abbreviated as PyMT or PyV MT. Col1a1$^{tmJae}$ homozygote males were crossed to C57BL/6 females to generate heterozygous females that were crossed to PyVT males to generate mice with normal and collagen dense mammary tissues carrying the polyoma transgene. Genotyping by PCR was performed on DNA extracted from tail biopsies (Wizard SV Genomic DNA Purification System, Promega, Madison, Wis.) using primers indicated in the strain information provided by The Jackson Laboratory. Mice were examined for palpable tumors starting at seven weeks of age and euthanized at 15 weeks or when the tumor burden became excessive.

Histology and Mammary Gland Whole Mounts. Selected mammary tissues and tumors were fixed in 4% paraformaldehyde in PBS followed by paraffin-embedding. Additionally, all tissues imaged with multiphoton microscopy were subsequently fixed and processed for histology. Tissue sections were stained with hematoxylin and eosin (H&E) with adjacent sections stained with the selective collagen stain, picrosirius red. Mammary whole mounts were prepared by fixing tissues in Carnoy's solution (10% glacial acetic acid/30% chloroform/60% absolute ethanol), followed by rehydration and staining with carmine alum. Tissues were then dehydrated, cleared with xylene, and mounted.

Multiphoton Laser-Scanning Microscopy (MPLSM). For live tissue imaging by multiphoton excitation (MPE) and second harmonic generation (SHG), mammary tumors were harvested and live tissue maintained in buffered media at 37° C. All tissues were imaged immediately following tissue harvest using an Optical Workstation[25] that was constructed around a Nikon Eclipse TE300. A 5 W mode-locked Ti:sapphire laser (Millennium/Tsunami, Spectra-Physics, Mountain View, Calif.) excitation source producing around 100 fs pulse widths and tuned to 890 nm was utilized to generate both MPE and SHG. The beam was focused onto the sample with a Nikon 60× Plan Apo water-immersion lens (N.A.=1.2). All SHG imaging was detected from the back-scattered SHG signal[48], and the presence of collagen confirmed in our tissues using fluorescence lifetime imaging microscopy (FLIM) on the same optical workstation, since the SHG from collagen has no lifetime. Furthermore, due to the fundamentally different physical behavior of MPE and SHG, signals could be discriminated by filtering the emission signal. We used a 464 nm (cut-on) long pass to isolate the emission from autofluorescence from the conserved 445 nm SHG emission. A 445 nm (narrow band pass) filter was therefore used to isolate the SHG emission. Acquisition was performed with WiscScan a software acquisition package developed at LOCI (Laboratory for Optical and Computational Instrumentation, University of Wisconsin, Madison, Wis.) and image analysis for MPE/SHG was performed with ImageJ and VisBio software. For TACS-1 image analysis additional surface rendering plug-ins for ImageJ were utilized (see http://rsb.info.nih.gov/ij/). For TACS-2 and -3, ImageJ was used to quantify the collagen fiber angle relative to the tumor. The tumor boundary was defined and the angle relative to the tangent of tumor boundary was measured every 10 microns as previously reported[25].

Fluorescence and Spectral Lifetime Imaging Microscopy (FLIM and SLIM). FLIM was performed on live tissue with the Optical workstation described above as previously described[25]. Briefly, the 5 W Ti:sapphire laser (Millennium/Tsunami, Spectra-Physics, Mountain View, Calif.) was tuned to 890 nm with the beam focused onto the sample with a Nikon 60× Plan Apo water-immersion lens (N.A.=1.2). Intensity and FLIM data were collected by a H7422 GaAsP photon-counting PMT (Hamamatsu, Bridgewater, N.J.) connected to a time correlated single photon counting (TCSPC) system (SPC-730, Becker & Hickl, Berlin, Germany). Multiphoton SLIM was performed using a second generation system that evolved from a previously described instrument 49 built around an inverted microscope (Eclipse TE2000, Nikon, Melville, N.Y.). Briefly, an 8-W solid-state Ti:Sapphire mode-locking laser (Coherent Mira, Coherent, Santa Clara, Calif.) was used to generate pulse widths of approximately 120 fs at a repetition rate of 76 MHz. Intensity and fluorescence lifetime data were collected over 16 individual 10 nm spectral-width channel using a 16-anode photon counting linear PMT array (PML-16, Becker & Hickl) connected to a TCSPC system (SPC-830, Becker&Hickl). Fluorescent lifetime analysis from FLIM and SLIM was carried out with SPCImage (Becker & Hickl) as well as with a LOCI created computational tool, SlimPlotter, which allows visualization and analysis of the lifetimes by spectral channel.

3D Invasion Assay. Uniform sized tumor explants were harvested from intact tumors using a tissue biopsy punch (3 mm diameter), rinsed with PBS (containing 100 units penicillin/100 ug streptomycin/0.25 ug/mL amphotericin B), and placed into 2.0 mg/mL collagen gels (BDBioscience, San Diego, Calif.) that were neutralized with 2×HEPES buffer. Tumors were maintained in collagen gels floated in DMEM containing 5% FBS, penicillin (100 units), streptomycin (100 ug), and amphotericin B (0.25 ug/mL) for 10 days over which time the number of distant multicellular colonies were counted.

Lung metastasis. Lungs from PyVT/wt and PyVT/Col1a1 mice (as well as wt/wt and wt/Col1a1 as negative controls) were harvested at 15 weeks, fixed in formalin, and processed for histology. Sections were cut every 50 μm through the entire tissue and sections stained with hematoxylin and eosin. Total lung metastases over all sections were then counted.

Isolation of tumor cells and migration assay. Tumors from PyVT/wt and PyVT/Col1a1 backgrounds we minced and digested with 2 mg/mL collagenase and 10 μg/mL hyaluronidase in DMEM containing penicillin (100 units), streptomycin (100 ug), and amphotericin B (0.25 ug/mL). Following gentle shaking at 37° C. for three hours, cell were pelleted, washed, and plated in DMEM containing 5% FBS. Thirty-six hours post-harvest the tumor cells were transferred in to Transwell plates (Corning Inc., Corning, N.Y.) using serum and soluable collagen containing media as the chemotractant Statistical Analysis. For multi-group comparisons, one-way Analysis of Variance (ANOVA) with a post-hoc Tukey-Kramer test was used. For two-group comparisons t-testing was performed.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

U.S. Pat. No. 6,687,000, issued on Feb. 3, 2004, relates to instrumentation and methods for characterizing properties of flourophores in samples, including fluorescent lifetimes and fluorescent lifetime related parameters, which is hereby incorporated by reference in its entirety. U.S. Patent publication No. 2008/0015448, published Jan. 17, 2008, relates to methods and systems for detecting, diagnosing and characterizing cancer using nonlinear optical techniques, which is hereby incorporated by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

1. McCormack, V. A. & dos Santos Silva, I. Breast density and parenchymal patterns as markers of breast cancer risk: a meta-analysis. *Cancer Epidemiol Biomarkers Prev* 15, 1159-69 (2006).
2. Boyd, N. F., Lockwood, G. A., Byng, J. W., Tritchler, D. L. & Yaffe, M. J. Mammographic densities and breast cancer risk. *Cancer Epidemiol Biomarkers Prev* 7, 1133-44. (1998).
3. Boyd, N. F., Martin, L. J., Stone, J., Greenberg, C., Minkin, S. & Yaffe, M. J. Mammographic densities as a marker of human breast cancer risk and their use in chemoprevention. *Curr Oncol Rep* 3, 314-21. (2001).
4. Boyd, N. F., Rommens, J. M., Vogt, K., Lee, V., Hopper, J. L., Yaffe, M. J. & Paterson, A. D. Mammographic breast density as an intermediate phenotype for breast cancer. *Lancet Oncol* 6, 798-808 (2005).
5. Alowami, S., Troup, S., Al-Haddad, S., Kirkpatrick, I. & Watson, P. H. Mammographic density is related to stroma and stromal proteoglycan expression. *Breast Cancer Res* 5, R129-35 (2003).
6. Ursin, G., Hovanessian-Larsen, L., Parisky, Y. R., Pike, M. C. & Wu, A. H. Greatly increased occurrence of breast cancers in areas of mammographically dense tissue. *Breast Cancer Res* 7, R605-8 (2005).
7. Rutter, C. M., Mandelson, M. T., Laya, M. B., Seger, D. J. & Taplin, S. Changes in breast density associated with initiation, discontinuation, and continuing use of hormone replacement therapy. *Jama* 285, 171-6. (2001).
8. Gill, J. K., Maskarinec, G., Pagano, I. & Kolonel, L. N. The association of mammographic density with ductal carcinoma in situ of the breast: the Multiethnic Cohort. *Breast Cancer Res* 8, R30 (2006).
9. Habel, L. A., Dignam, J. J., Land, S. R., Salane, M., Capra, A. M. & Julian, T. B. Mammographic density and breast cancer after ductal carcinoma in situ. *J Natl Cancer Inst* 96, 1467-72 (2004).
10. Aiello, E. J., Buist, D. S., White, E. & Porter, P. L. Association between mammographic breast density and breast cancer tumor characteristics. *Cancer Epidemiol Biomarkers Prev* 14, 662-8 (2005).
11. Hawes, D., Downey, S., Pearce, C. L., Bartow, S., Wan, P., Pike, M. C. & Wu, A. H. Dense breast stromal tissue shows greatly increased concentration of breast epithelium but no increase in its proliferative activity. *Breast Cancer Res* 8, R24 (2006).
12. Li, T., Sun, L., Miller, N., Nicklee, T., Woo, J., Hulse-Smith, L., Tsao, M. S., Khokha, R., Martin, L. & Boyd, N. The association of measured breast tissue characteristics with mammographic density and other risk factors for breast cancer. *Cancer Epidemiol Biomarkers Prev* 14, 343-9 (2005).
13. Guo, Y. P., Martin, L. J., Hanna, W., Banerjee, D., Miller, N., Fishell, E., Khokha, R. & Boyd, N. F. Growth factors and stromal matrix proteins associated with mammographic densities. *Cancer Epidemiol Biomarkers Prev* 10, 243-8. (2001).
14. Barcellos-Hoff, M. H., Aggeler, J., Ram, T. G. & Bissell, M. J. Functional differentiation and alveolar morphogenesis of primary mammary cultures on reconstituted basement membrane. *Development* 105, 223-35. (1989).
15. Keely, P., Fong, A., Zutter, M. & Santoro, S. Alteration of collagen-dependent adhesion, motility, and morphogenesis by the expression of antisense a2 integrin mRNA in mammary cells. *J Cell Science* 108, 595-607 (1995).
16. Tlsty, T. D. & Hein, P. W. Know thy neighbor: stromal cells can contribute oncogenic signals. *Curr Opin Genet Dev* 11, 54-9 (2001).
17. Noel, A. & Foidart, J. M. The role of stroma in breast carcinoma growth in vivo. *J Mammary Gland Biol Neoplasia* 3, 215-25. (1998).
18. Elenbaas, B., Spirio, L., Koerner, F., Fleming, M. D., Zimonjic, D. B., Donaher, J. L., Popescu, N. C., Hahn, W. C. & Weinberg, R. A. Human breast cancer cells generated by oncogenic transformation of primary mammary epithelial cells. *Genes Dev* 15, 50-65. (2001).
19. Orimo, A., Gupta, P. B., Sgroi, D. C., Arenzana-Seisdedos, F., Delaunay, T., Naeem, R., Carey, V. J., Richardson, A. L. & Weinberg, R. A. Stromal fibroblasts present in invasive human breast carcinomas promote tumor growth and angiogenesis through elevated SDF-1/CXCL12 secretion. *Cell* 121, 335-48 (2005).
20. Iyengar, P., Espina, V., Williams, T. W., Lin, Y., Berry, D., Jelicks, L. A., Lee, H., Temple, K., Graves, R., Pollard, J., Chopra, N., Russell, R. G., Sasisekharan, R., Trock, B. J., Lippman, M., Calvert, V. S., Petricoin, E. F., III, Liotta, L., Dadachova, E., Pestell, R. G., Lisanti, M. P., Bonaldo, P. & Scherer, P. E. Adipocyte-derived collagen VI affects early mammary tumor progression in vivo, demonstrating a critical interaction in the tumor/stroma microenvironment. *J. Clin. Invest.* 115, 1163-1176 (2005).
21. White, D. E., Kurpios, N. A., Zuo, D., Hassell, J. A., Blaess, S., Mueller, U. & Muller, W. J. Targeted disruption of beta1-integrin in a transgenic mouse model of human breast cancer reveals an essential role in mammary tumor induction. *Cancer Cell* 6, 159-70 (2004).
22. Paszek, M. J., Zahir, N., Johnson, K. R., Lakins, J. N., Rozenberg, G. I., Gefen, A., Reinhart-King, C. A., Margulies, S. S., Dembo, M., Boettiger, D., Hammer, D. A. & Weaver, V. M. Tensional homeostasis and the malignant phenotype. Cancer Cell 8, 241-54 (2005).
23. Wozniak, M. A., Desai, R., Solski, P. A., Der, C. J. & Keely, P. J. ROCK-generated contractility regulates breast epithelial cell differentiation in response to the physical properties of a three-dimensional collagen matrix. *J Cell Biol* 163, 583-95 (2003).
24. Liu, X., Wu, H., Byrne, M., Jeffrey, J., Krane, S. & Jaenisch, R. A targeted mutation at the known collagenase cleavage site in mouse type I collagen impairs tissue remodeling. *J Cell Biol* 130, 227-37 (1995).
25. Provenzano, P. P., Eliceiri, K. W., Campbell, J. M., Inman, D. R., White, J. G. & Keely, P. J. Collagen reorganization at the tumor-stromal interface facilitates local invasion. *BMC Medicine* 4:38, 2006.
26. Lin, E. Y., Jones, J. G., Li, P., Zhu, L., Whitney, K. D., Muller, W. J. & Pollard, J. W. Progression to malignancy in the polyoma middle T oncoprotein mouse breast cancer model provides a reliable model for human diseases. *Am J Pathol* 163, 2113-26 (2003).

27. Wang, W., Wyckoff, J. B., Frohlich, V. C., Oleynikov, Y., Huttelmaier, S., Zavadil, J., Cermak, L., Bottinger, E. P., Singer, R. H., White, J. G., Segall, J. E. & Condeelis, J. S. Single cell behavior in metastatic primary mammary tumors correlated with gene expression patterns revealed by molecular profiling. *Cancer Res* 62, 6278-88 (2002).

28. Zipfel, W. R., Williams, R. M., Christie, R., Nikitin, A. Y., Hyman, B. T. & Webb, W. W. Live tissue intrinsic emission microscopy using multiphoton-excited native fluorescence and second harmonic generation. *Proc Natl Acad Sci USA* 100, 7075-80 (2003).

29. Zoumi, A., Yeh, A. & Tromberg, B. J. Imaging cells and extracellular matrix in vivo by using second-harmonic generation and two-photon excited fluorescence. *Proc Natl Acad Sci USA* 99, 11014-9 (2002).

30. Brown, E., McKee, T., diTomaso, E., Pluen, A., Seed, B., Boucher, Y. & Jain, R. K. Dynamic imaging of collagen and its modulation in tumors in vivo using second-harmonic generation. *Nat Med* 9, 796-800 (2003).

31. Pradhan, A., Pal, P., Durocher, G., Villeneuve, L., Balassy, A., Babai, F., Gaboury, L. & Blanchard, L. Steady state and time-resolved fluorescence properties of metastatic and non-metastatic malignant cells from different species. *J Photochem Photobiol B* 31, 101-12 (1995).

32. Bavik, C., Coleman, I., Dean, J. P., Knudsen, B., Plymate, S. & Nelson, P. S. The gene expression program of prostate fibroblast senescence modulates neoplastic epithelial cell proliferation through paracrine mechanisms. *Cancer Res* 66, 794-802 (2006).

33. Allinen, M., Beroukhim, R., Cai, L., Brennan, C., Lahti-Domenici, J., Huang, H., Porter, D., Hu, M., Chin, L., Richardson, A., Schnitt, S., Sellers, W. R. & Polyak, K. Molecular characterization of the tumor microenvironment in breast cancer. *Cancer Cell* 6, 17-32 (2004).

34. Chung, L. W., Baseman, A., Assikis, V. & Zhau, H. E. Molecular insights into prostate cancer progression: the missing link of tumor microenvironment. *J Urol* 173, 10-20 (2005).

35. De Wever, O. & Mareel, M. Role of tissue stroma in cancer cell invasion. *J Pathol* 200, 429-47 (2003).

36. Condeelis, J., Singer, R. H. & Segall, J. E. THE GREAT ESCAPE: When Cancer Cells Hijack the Genes for Chemotaxis and Motility. *Annual Review of Cell and Developmental Biology* 21, 695-718 (2005).

37. Parr, C., Watkins, G., Mansel, R. E. & Jiang, W. G. The Hepatocyte Growth Factor Regulatory Factors in Human Breast Cancer. *Clin Cancer Res* 10, 202-211 (2004).

38. Sachdev, D. & Yee, D. The IGF system and breast cancer. *Endocr Relat Cancer* 8, 197-209 (2001).

39. Surmacz, E. Function of the IGF-I receptor in breast cancer. *J Mammary Gland Biol Neoplasia* 5, 95-105 (2000).

40. Byrne, C., Colditz, G. A., Willett, W. C., Speizer, F. E., Pollak, M. & Hankinson, S. E. Plasma insulin-like growth factor (IGF) I, IGF-binding protein 3, and mammographic density. *Cancer Res* 60, 3744-8 (2000).

41. Boyd, N. F., Stone, J., Martin, L. J., Jong, R., Fishell, E., Yaffe, M., Hammond, G. & Minkin, S. The association of breast mitogens with mammographic densities. *Br J Cancer* 87, 876-82 (2002).

42. Benlimame, N., He, Q., Jie, S., Xiao, D., Xu, Y. J., Loignon, M., Schlaepfer, D. D. & Alaoui-Jamali, M. A. FAK signaling is critical for ErbB-2/ErbB-3 receptor cooperation for oncogenic transformation and invasion. *J Cell Biol* 171, 505-16 (2005).

43. Aplin, A. E. & Juliano, R. L. Integrin and cytoskeletal regulation of growth factor signaling to the MAP kinase pathway. *J Cell Sci* 112 (Pt 5), 695-706 (1999).

44. Baron, V., Calleja, V., Ferrari, P., Alengrin, F. & Van Obberghen, E. p125Fak focal adhesion kinase is a substrate for the insulin and insulin-like growth factor-I tyrosine kinase receptors. *J Biol Chem* 273, 7162-8 (1998).

45. Ishizawar, R. & Parsons, S. J. c-Src and cooperating partners in human cancer. *Cancer Cell* 6, 209-14 (2004).

46. Hauck, C. R., Sieg, D. J., Hsia, D. A., Loftus, J. C., Gaarde, W. A., Monia, B. P. & Schlaepfer, D. D. Inhibition of focal adhesion kinase expression or activity disrupts epidermal growth factor-stimulated signaling promoting the migration of invasive human carcinoma cells. *Cancer Res* 61, 7079-90 (2001).

47. Sieg, D. J., Hauck, C. R., Ilic, D., Klingbeil, C. K., Schaefer, E., Damsky, C. H. & Schlaepfer, D. D. FAK integrates growth-factor and integrin signals to promote cell migration. *Nat Cell Biol* 2, 249-56 (2000).

48. Williams, R. M., Zipfel, W. R. & Webb, W. W. Interpreting second-harmonic generation images of collagen I fibrils. *Biophys J* 88, 1377-86 (2005).

49. Bird, D. K., Eliceiri, K. W., Fan, C. H. & White, J. G. Simultaneous two-photon spectral and lifetime fluorescence microscopy. *Appl Opt* 43, 5173-82 (2004).

50. Huang, S., Heikal, A. A. & Webb, W. W. Two-photon fluorescence spectroscopy and microscopy of NAD(P)H and flavoprotein. *Biophys J* 82, 2811-25 (2002).

We claim:

1. A method of evaluating a test tissue sample for the diagnosis of cancer, said method comprising the steps of:
   a) providing the test tissue sample from a test subject, wherein said test tissue sample comprises a mammary tissue component;
   b) generating a test image or test imaging data from the test tissue sample using a nonlinear optical imaging technique;
   c) analyzing said test image or test imaging data of the test tissue sample by measuring fluorescence intensities, fluorescence lifetime values or both from endogenous FAD in said test tissue sample;
   d) comparing said test image or test imaging data with a reference image or reference imaging data corresponding to endogenous FAD in one or more reference tissues; and
   d) identifying the presence of invasive or metastatic cells relative to non-invasive cells or normal cells within the test tissue sample, thereby evaluating said test tissue sample for the diagnosis of cancer.

2. The method of claim 1 wherein said nonlinear optical imaging technique is selected from the group consisting of multiphoton microscopy (MPM), multiphoton fluorescent lifetime imaging microscopy (FLIM), second harmonic generation, and multiphoton spectral lifetime imaging microscopy (SLIM).

3. The method of claim 1 wherein said test tissue sample is a breast tissue sample.

4. The method of claim 1 wherein said test tissue sample is intact and non-fixed.

5. The method of claim 1 wherein said test image or test imaging data from the test tissue sample comprises one or more of:
   a. a FAD intensity image of said test sample;
   b. a FAD fluorescence lifetime image of said test sample; and
   c. a second harmonic generation intensity image of said test sample.

6. The method of claim 1 wherein said test image or test imaging data from the test tissue sample comprises a plurality of fluorescence lifetime images corresponding to fluorescence from said test sample having different wavelengths.

7. The method of claim 1 wherein said comparing step further comprises one or more comparison steps selected from the group consisting of:
 a. comparing at least a portion of said fluorescence intensities to a reference fluorescence intensity value or set of reference fluorescence intensity values corresponding to endogenous FAD in said one or more reference tissues; and
 b. comparing at least a portion of said fluorescence lifetime values to a reference fluorescence lifetime value or set of reference fluorescence lifetime values corresponding to endogenous FAD in said one or more reference tissues.

8. The method of claim 7 wherein said reference fluorescence intensity value or set of reference fluorescence intensity values, said reference fluorescence lifetime values or set of reference fluorescence lifetime values or both are determined from one or more reference tissues having a normal condition.

9. The method of claim 7 wherein said reference fluorescence intensity value or set of reference fluorescence intensity values, said reference fluorescence lifetime values or set of reference fluorescence lifetime values or both are determined from one or more reference tissues having a disease condition.

10. The method of claim 7 wherein said test tissue sample provides one or more first stromal or epithelial regions suspected of a cancerous condition; wherein the test tissue sample also serves as said one or more reference tissues, wherein said reference fluorescence intensity value or set of reference fluorescence intensity values, said reference fluorescence lifetime values or set of reference fluorescence lifetime values or both are determined from one or more second stromal or epithelial regions of said test sample having a normal condition.

11. The method of claim 7 wherein said test tissue sample provides one or more stromal or epithelial regions suspected of a cancerous condition; wherein the test tissue sample also serves as said one or more reference tissues, wherein said reference fluorescence intensity value or set of reference fluorescence intensity values, said reference fluorescence lifetime values or set of reference fluorescence lifetime values or both are determined from one or more tumor regions of said test tissue sample.

12. The method of claim 7 wherein said test tissue sample provides one or more first tumor regions suspected of an invasive state; wherein the test tissue sample also serves as said one or more reference tissues, wherein said reference fluorescence intensity value or set of reference fluorescence intensity values, said reference fluorescence lifetime values or set of reference fluorescence lifetime values or both are determined from one or more second tumor regions having a noninvasive state.

13. The method of claim 7 further comprising the steps of:
 a. determining the percentage differences between at least a portion of said fluorescence intensities of said endogenous FAD in said test tissue sample and said reference fluorescence intensity value or set of reference fluorescence intensity values; and
 b. identifying the presence of invasive or metastatic cells in said test tissue upon observing a percentage difference between at least a portion of said fluorescence intensities and said reference fluorescence intensity value or set of reference fluorescence intensity values greater than or equal to 50%.

14. The method of claim 7 further comprising the steps of:
 a. fitting temporal profiles of FAD fluorescence in said test tissue sample to the expression:

$$I_f(t) = \sum_{i=0}^{n} a_i \exp^{(-t/\tau_i)} + c = a_1 \exp^{-t/\tau_1} + a_2 \exp^{-t/\tau_2} + a_3 \exp^{-t/\tau_3} + \ldots + c;$$

b. determining one or more fluorescence lifetime values selected from the group consisting of:
  i. a first component of the fluorescent lifetime ($\tau_1$) of FAD in said test tissue sample;
  ii. a second component of the fluorescent lifetime ($\tau_2$) of FAD in said test tissue sample; and
  iii. weighted mean values ($\tau_m$) of the fluorescent lifetime of said endogenous FAD in said test tissue sample.

15. The method of claim 14 further comprising the step of determining the differences of the first components of the fluorescent lifetime ($\tau_1$), the second components of the fluorescent lifetime ($\tau_2$) or the weighted mean values ($\tau_m$) of the fluorescent lifetime and said reference fluorescence lifetime value or set of reference fluorescence lifetime values.

16. The method of claim 14 further comprising one or more additional steps of:
 a. determining the percentage differences between at least a portion of the first components ($\tau_1$), the second components ($\tau_2$) or the weighted mean values ($\tau_m$) and said reference fluorescence lifetime value or set of reference fluorescence lifetime values; and
 b. identifying the presence of invasive or metastatic cells in said test tissue upon observing a difference between at least a portion of the first components ($\tau_1$), the second components ($\tau_2$) or the weighted mean values ($\tau_m$) and said reference fluorescence lifetime value or set of reference fluorescence lifetime values greater than or equal to 40% for $\tau_1$, 10% for $\tau_2$, or 50% for $\tau_m$.

17. The method of claim 1 wherein said test tissue sample is from a first species and said one or more reference tissues are from said first species or from a second species that is different from said first species.

18. The method of claim 17 wherein said first species is human.

19. The method of claim 1 wherein said step of generating a test image or test imaging data from the test tissue sample comprises exposing said test tissue sample to electromagnetic radiation having wavelengths selected over the range of 860 nm to 940 nm.

20. The method of claim 1 wherein said step of generating a test image or test imaging data from the test tissue sample comprises detecting fluorescence from said test tissue sample having wavelengths selected over the range of 510 nm to 550 nm.

21. The method of claim 1 further comprising the step of generating a second harmonic generation image or image data of said test tissue sample, wherein said second harmonic generation image or image data provides an image of collagen in said test tissue sample.

22. The method of claim 1 comprising: a method of identifying the presence of cancer cells in said test tissue sample; a method of distinguishing benign and invasive cancer cells in said test tissue sample; or a method of characterizing the stage of cancer in said test tissue sample.

23. A method for evaluating a tumor in a tissue sample for invasiveness or metastatic potential, said method comprising the steps of:
   a. obtaining a plurality of test images from said test tissue sample using one or more nonlinear optical imaging techniques; said test images comprising a multiphoton intensity image of said test tissue sample and a fluorescence lifetime image of said test tissue sample;
   b. analyzing said multiphoton intensity image by measuring fluorescence intensities of endogenous FAD in said test tissue sample;
   c. analyzing said fluorescence lifetime image by measuring fluorescent lifetime values from endogenous FAD in said test tissue sample;
   d. comparing said fluorescence intensities and fluorescent lifetime values of said test tissue to a set of reference values corresponding to endogenous FAD in one or more reference tissues; and
   e. identifying the presence of invasive or metastatic cells relative to non-invasive cells or normal cells within the test tissue sample; thereby evaluating a tumor for invasiveness or metastatic potential.

24. The method of claim 23 wherein said tumor is an epithelial tumor.

25. A method of locating a tissue region associated with a cancer risk, said method comprising the steps of:
   a. providing a test tissue sample;
   b. generating a test image or test imaging data from the test tissue sample using a nonlinear optical imaging technique,
   c. analyzing said test image or test imaging data of the test tissue sample by measuring fluorescence intensities, fluorescent lifetime values or both from endogenous FAD in said test tissue sample;
   d. comparing at least a portion of said fluorescence intensities or fluorescent lifetime values to a reference value or set of reference values corresponding to endogenous FAD in one or more reference tissues; and
   e. identifying fluorescence intensities or fluorescent lifetime values that are different from said reference value or set of reference values; thereby identifying the presence of invasive or metastatic cells relative to non-invasive cells or normal cells within the test tissue sample, and spatially orienting said fluorescence intensities or fluorescent lifetime values that are different from said reference value or set of reference values with respect to the corresponding tissue sample or a three-dimensional representation of the tissue sample; thereby locating said tissue region associated with said cancer risk.

26. The method of claim 25 wherein said tissue region associated with said cancer risk is a region having invading metastatic tumor cells.

27. A method of evaluating a test tissue sample for the diagnosis of cancer, said method comprising the steps of:
   A. providing the test tissue sample from a test subject, wherein said test tissue sample comprises a mammary tissue component;
   B. generating a test image or test imaging data from the test tissue sample using a nonlinear optical imaging technique; and
   C. analyzing said test image or test imaging data of the test tissue sample by:
      i. measuring fluorescence intensities, fluorescence lifetime values or both from endogenous FAD in said test tissue sample,
      ii. comparing at least a portion of said fluorescence intensities, said fluorescence lifetime values or both with a reference value or set of reference values corresponding to endogenous FAD in one or more reference tissues; and
      i. identifying the presence of invasive or metastatic cells in said test tissue sample upon observing:
         a. a percentage difference greater than or equal to 50% between at least a portion of said fluorescence intensities of said endogenous FAD in said test tissue sample and a reference fluorescence intensity value or set of reference fluorescence intensity values corresponding to endogenous FAD in one or more reference tissues; or
         b. a temporal profile of FAD fluorescence in said test tissue sample fitted to the expression:

$$I_f(t) = \sum_{i=0}^{n} a_i \exp^{(-t/\tau_i)} + c = a_1 \exp^{-t/\tau_1} + a_2 \exp^{-t/\tau_2} + a_3 \exp^{-t/\tau_3} + \ldots + c;$$

and where there is a percentage difference greater than or equal to 40% for $\tau_1$, 10% for $\tau_2$, or 50% for $\tau_m$ between at least a portion of first components ($\tau_1$), second components ($\tau_2$) or weighted mean values ($\tau_m$) of said fluorescent lifetime value of said endogenous FAD in said test tissue sample and a reference fluorescence lifetime value or set of reference fluorescence lifetime values corresponding to endogenous FAD in one or more reference tissues, thereby evaluating said test tissue sample for the diagnosis of cancer.

* * * * *